(12) United States Patent
Ito et al.

(10) Patent No.: US 12,721,535 B2
(45) Date of Patent: Sep. 1, 2026

(54) PULSE TRANSIT TIME MEASUREMENT DEVICE AND BLOOD PRESSURE MEASUREMENT DEVICE

(71) Applicants: OMRON HEALTHCARE Co., Ltd., Kyoto (JP); OMRON Corporation, Kyoto (JP)

(72) Inventors: Akito Ito, Kyoto (JP); Yasuhiro Kawabata, Kyoto (JP); Kenji Fujii, Kyoto (JP); Naomi Matsumura, Kyoto (JP); Reiji Fujita, Kyoto (JP)

(73) Assignees: OMRON HEALTHCARE CO., LTD., Kyoto (JP); OMRON CORPORATION, Kyoto (JP)

( * ) Notice: Subject to any disclaimer, the term of this patent is extended or adjusted under 35 U.S.C. 154(b) by 961 days.

(21) Appl. No.: 17/178,850

(22) Filed: Feb. 18, 2021

(65) Prior Publication Data

US 2021/0169347 A1 Jun. 10, 2021

Related U.S. Application Data

(63) Continuation of application No. PCT/JP2019/029018, filed on Jul. 24, 2019.

(30) Foreign Application Priority Data

Aug. 23, 2018 (JP) ................................ 2018-156199

(51) Int. Cl.
*A61B 5/282* (2021.01)
*A61B 5/00* (2006.01)
(Continued)

(52) U.S. Cl.
CPC .......... *A61B 5/025* (2013.01); *A61B 5/02125* (2013.01); *A61B 5/02233* (2013.01);
(Continued)

(58) Field of Classification Search
CPC . A61B 5/025; A61B 5/02125; A61B 5/02233; A61B 5/256; A61B 5/282;
(Continued)

(56) References Cited

U.S. PATENT DOCUMENTS 6,202,510 B1 * 3/2001 Kupelian ................ B29C 73/08 81/15.5
2001/0051773 A1 12/2001 Oka
(Continued)

FOREIGN PATENT DOCUMENTS

CA 2776204 A1 7/2012
CN 102008296 A 4/2011
(Continued)

OTHER PUBLICATIONS

Notice of Reasons for Refusal issued Jun. 6, 2023 in corresponding Japanese Patent Application No. 2022-139497, with English language translation.

(Continued)

*Primary Examiner* — Eun Hwa Kim
*Assistant Examiner* — Ana Veruska Guerrero
(74) *Attorney, Agent, or Firm* — Wenderoth, Lind & Ponack, L.L.P.

(57) ABSTRACT

A pulse transit time measurement device according to an aspect includes: a belt unit; a plurality of first electrodes and second electrodes provided on the belt unit; a third electrode provided on the belt unit; a first electrocardiographic signal acquisition unit that acquires a first electrocardiographic signal of a user using the plurality of first electrodes; a second electrocardiographic signal acquisition unit that acquires a second electrocardiographic signal of the user with the second electrode and the third electrode; a feature amount parameter calculation unit that calculates a feature amount parameter related to a waveform feature point of the (Continued)

first electrocardiographic signal on the basis of a waveform feature point of the second electrocardiographic signal; a pulse wave signal acquisition unit that acquires a pulse wave signal representing a pulse wave of the user; and a pulse transit time calculation unit that detects a waveform feature point.

22 Claims, 11 Drawing Sheets

(51) Int. Cl.

| | |
|---|---|
| ***A61B 5/02*** | (2006.01) |
| ***A61B 5/021*** | (2006.01) |
| ***A61B 5/022*** | (2006.01) |
| ***A61B 5/025*** | (2006.01) |
| ***A61B 5/256*** | (2021.01) |
| ***A61B 5/352*** | (2021.01) |
| *A61B 5/024* | (2006.01) |
| *A61B 5/0245* | (2006.01) |
| *A61B 5/026* | (2006.01) |
| *A61B 5/24* | (2021.01) |
| *A61B 5/25* | (2021.01) |
| *A61B 5/251* | (2021.01) |
| *A61B 5/28* | (2021.01) |
| *A61B 5/307* | (2021.01) |
| *A61B 5/308* | (2021.01) |
| *A61B 5/318* | (2021.01) |
| *A61B 5/335* | (2021.01) |
| *A61B 5/346* | (2021.01) |
| *A61B 5/349* | (2021.01) |
| *A61B 5/36* | (2021.01) |

(52) U.S. Cl.

CPC .............. *A61B 5/256* (2021.01); *A61B 5/282* (2021.01); *A61B 5/352* (2021.01); *A61B 5/6831* (2013.01); *A61B 5/0048* (2013.01); *A61B 5/0053* (2013.01); *A61B 5/0082* (2013.01); *A61B 5/02* (2013.01); *A61B 5/021* (2013.01); *A61B 5/022* (2013.01); *A61B 5/024* (2013.01); *A61B 5/0245* (2013.01); *A61B 5/026* (2013.01); *A61B 5/24* (2021.01); *A61B 5/25* (2021.01); *A61B 5/251* (2021.01); *A61B 5/28* (2021.01); *A61B 5/307* (2021.01); *A61B 5/308* (2021.01); *A61B 5/318* (2021.01); *A61B 5/335* (2021.01); *A61B 5/346* (2021.01); *A61B 5/349* (2021.01); *A61B 5/36* (2021.01); *A61B 5/68* (2013.01); *A61B 5/6801* (2013.01); *A61B 5/6802* (2013.01); *A61B 5/6824* (2013.01); *A61B 5/683* (2013.01); *A61B 2562/0209* (2013.01); *A61B 2562/06* (2013.01); *A61B 2562/22* (2013.01)

(58) Field of Classification Search

CPC ..... A61B 5/352; A61B 5/6831; A61B 5/0048; A61B 5/0053; A61B 5/0082; A61B 5/02; A61B 5/021; A61B 5/022; A61B 5/024; A61B 5/0245; A61B 5/026; A61B 5/24; A61B 5/25; A61B 5/251; A61B 5/28; A61B 5/307; A61B 5/308; A61B 5/318; A61B 5/335; A61B 5/346; A61B 5/349; A61B 5/68; A61B 5/6801; A61B 5/6802; A61B 5/6824; A61B 5/683; A61B 2562/0209; A61B 2562/06; A61B 2562/22; A61B 5/36

See application file for complete search history.

(56) References Cited

U.S. PATENT DOCUMENTS

| | | | | |
|---|---|---|---|---|
| 2003/0120164 | A1* | 6/2003 | Nielsen | A61B 5/742 600/513 |
| 2006/0009691 | A1* | 1/2006 | Yeo | A61B 5/0245 600/521 |
| 2012/0283583 | A1* | 11/2012 | Batkin | A61B 5/025 600/499 |
| 2014/0012146 | A1 | 1/2014 | Fukuda | |
| 2015/0065891 | A1 | 3/2015 | Wiesel | |
| 2015/0366473 | A1 | 12/2015 | Shimuta et al. | |
| 2016/0081565 | A1 | 3/2016 | Kinoshita et al. | |
| 2016/0089081 | A1 | 3/2016 | Morris et al. | |
| 2017/0245773 | A1* | 8/2017 | Wiesel | A61B 5/361 |
| 2018/0014742 | A1 | 1/2018 | Iwawaki | |
| 2018/0303353 | A1* | 10/2018 | Baxi | A61B 5/02125 |
| 2019/0209031 | A1 | 7/2019 | Ariyama et al. | |

FOREIGN PATENT DOCUMENTS

| | | | | |
|---|---|---|---|---|
| CN | 103519794 | A | 1/2014 | |
| CN | 105007809 | A | 10/2015 | |
| CN | 105358049 | | 2/2016 | |
| CN | 106714674 | A | 5/2017 | |
| EP | 581073 | A2 * | 2/1994 | A61B 5/0006 |
| EP | 1161920 | A2 | 12/2001 | |
| EP | 2962633 | A1 | 1/2016 | |
| GB | 2490594 | A | 11/2012 | |
| JP | 10-302188 | | 11/1998 | |
| JP | 2001-346769 | A | 12/2001 | |
| JP | 2007-504917 | A | 3/2007 | |
| JP | 2011-156194 | A | 8/2011 | |
| JP | 2014-012072 | A | 1/2014 | |
| JP | 2016154754 | A * | 9/2016 | A61B 5/02 |
| JP | 6202510 | B1 * | 9/2017 | A61B 5/02 |
| WO | 2014/132713 | A1 | 9/2014 | |
| WO | WO-2016040264 | A1 * | 3/2016 | A61B 5/02125 |
| WO | 2016/053751 | A1 | 4/2016 | |
| WO | 2016/136135 | A1 | 9/2016 | |
| WO | 2018/043692 | | 3/2018 | |
| WO | WO-2018043692 | A1 * | 3/2018 | A61B 5/0082 |

OTHER PUBLICATIONS

1st Review Opinion Notice issued Mar. 2, 2023 in corresponding Chinese Patent Application No. 201980048514.5, with English language translation.

International Preliminary Report on Patentability issued Feb. 25, 2021 in International (PCT) Application No. PCT/JP2019/029018.

* cited by examiner

PULSE TRANSIT TIME MEASUREMENT DEVICE AND BLOOD PRESSURE MEASUREMENT DEVICE

CROSS-REFERENCE TO RELATED APPLICATIONS

This application is the U.S. national stage application filed pursuant to 35 U.S.C. 365(c) and 120 as a continuation of International Patent Application No. PCT/JP2019/029018, filed Jul. 24, 2019, which application claims priority from Japanese Patent Application No. 2018-156199, filed Aug. 23, 2018, which applications are incorporated herein by reference in their entireties.

TECHNICAL FIELD

The present invention relates to a pulse transit time measurement device that non-invasively measures pulse transit time and a blood pressure measurement device using the pulse transit time measurement device.

BACKGROUND ART

It is known that there is a correlation between blood pressure and a pulse transit time (PTT), which is a time required for a pulse wave to propagate between two points in an artery. A blood pressure measurement device utilizing the correlation described above measures a pulse transit time of a user (subject) and calculates a blood pressure value of the user, using the measured pulse transit time and a blood pressure calculation equation representing the correlation described above.

As a method for measuring the pulse transit time, there is known a method of measuring and acquiring an electrocardiographic signal and a pulse wave signal representing pulse waves at a specific site (for example, ears, upper arms, and the like) of the user and calculating the pulse transit time on the basis of the acquired electrocardiographic signal and pulse wave signal. In this method, the electrocardiographic signal is generally acquired using a plurality of electrodes disposed on the body so as to sandwich the heart of the user.

However, Patent Document 1 discloses that electrocardiographic signals can be acquired at any site (for example, an upper arm) of a user.

CITATION LIST

Patent Literature

Patent Document 1: JP 2007-504917 T

SUMMARY OF INVENTION

Technical Problem

However, in a method for acquiring electrocardiographic signals using a plurality of electrodes arranged at a single site of a user as disclosed in Patent Document 1, since the signal representing the electrical activity of the heart is small and is easily confused with noise, and the electrocardiographic waveform is different depending on the combination of electrodes, it is difficult to acquire accurate electrocardiographic information. Thus, when the pulse transit time is calculated on the basis of electrocardiographic signals acquired using a plurality of electrodes disposed at a single site of a user, the drive timing of the heart may not be detected correctly and the pulse transit time may not be accurately measured.

The present invention has been made in view of the above circumstances, and an object of the present invention is to provide a pulse transit time measurement device capable of measuring the pulse transit time more accurately and a blood pressure measurement device using the pulse transit time measurement device.

Solution to Problem

The present invention adopts the following configurations in order to solve the above problems.

A pulse transit time measurement device according to an aspect includes: a belt unit wound around a target measurement site of a user; a plurality of first electrodes provided on an inner circumferential surface of the belt unit; a second electrode provided on the inner circumferential surface of the belt unit; a third electrode provided on an outer circumferential surface of the belt unit; a first electrocardiographic signal acquisition unit that acquires a first electrocardiographic signal of the user using the plurality of first electrodes; a second electrocardiographic signal acquisition unit that acquires a second electrocardiographic signal of the user using the second electrode and the third electrode in a period; a feature amount parameter calculation unit that calculates a feature amount parameter related to a waveform feature point of the first electrocardiographic signal acquired in the period based on a waveform feature point of the second electrocardiographic signal; a pulse wave signal acquisition unit that includes a pulse wave sensor provided in the belt unit and acquires a pulse wave signal representing a pulse wave of the user using the pulse wave sensor; and a pulse transit time calculation unit that detects a waveform feature point of the first electrocardiographic signal acquired later than the period using the feature amount parameter and calculates a pulse transit time based on a time difference between the waveform feature point of the first electrocardiographic signal that is detected and a waveform feature point of the pulse wave signal.

According to the configuration above, for example, when the belt unit is wound around the upper left arm of the user, the first electrode and the second electrode contact the upper left arm. When the user touches the third electrode with the right hand, a state in which the second electrode and the third electrode are positioned so as to sandwich the heart is created. Since the second electrocardiographic signal is acquired using the second electrode and the third electrode arranged so as to sandwich the heart, the second electrocardiographic signal is more accurate than the first electrocardiographic signal acquired using the first electrode disposed on the upper left arm. The first electrocardiographic signal and the second electrocardiographic signal are acquired simultaneously, and a feature amount parameter related to a waveform feature point of the first electrocardiographic signal is calculated on the basis of a waveform feature point of the second electrocardiographic signal. Then, when measuring the pulse transit time, the first electrocardiographic signal and the pulse wave signal are acquired, a waveform feature point of the first electrocardiographic signal is detected using the feature amount parameter, and a time difference between the detected waveform feature point of the first electrocardiographic signal and the waveform feature point of the pulse wave signal is calculated. By using the feature amount parameter calculated in advance, the waveform feature point (for example, a peak point corresponding to the R-wave) of the first electrocardiographic signal that is considered as the drive timing of the heart can be detected correctly and the pulse transit time can be measured accurately.

In one aspect, the feature amount parameter calculation unit may detect a peak with a maximum amplitude of the first electrocardiographic signal in a time range determined based on the waveform feature point of the second electrocardiographic signal and acquire an amplitude value of the peak that is detected or a sign of the amplitude value as the feature amount parameter. According to this configuration, the waveform feature point of the first electrocardiographic signal for calculating the pulse transit time can be detected correctly.

In one aspect, the second electrode may be one of the plurality of first electrodes. According to this configuration, it is not necessary to provide a dedicated electrode which comes into contact with the target measurement site, for acquiring the second electrocardiographic signal. As a result, the manufacturing cost can be reduced.

In one aspect, the above described pulse transit time measurement device may further include an electrode selection unit that selects two first electrodes that provide the first electrocardiographic signal having a greatest amplitude of an R-wave among the plurality of first electrodes, and the first electrocardiographic signal acquisition unit may acquire the first electrocardiographic signal based on a potential difference between the two first electrodes that are selected.

According to the configuration described above, the time of the R-wave peak point (the peak point corresponding to the R-wave) of the first electrocardiographic signal can be identified accurately. As a result, the pulse transit time can be measured more accurately.

A blood pressure measurement device according to an aspect includes: the above-described pulse transit time measurement device; and a first blood pressure value calculation unit calculating a first blood pressure value based on the pulse transit time that is calculated. According to the configuration described above, since the pulse transit time can be measured for each beat, it is possible to obtain a blood pressure value for each beat.

In an aspect, the blood pressure measurement device may further include a pressing cuff provided in the belt unit; a fluid supply unit supplying a fluid to the pressing cuff; a pressure sensor detecting pressure in the pressing cuff; and a second blood pressure value calculation unit calculating a second blood pressure value based on an output of the pressure sensor.

According to the configuration described above, continuous blood pressure measurement wherein a blood pressure value is obtained for each beat and blood pressure measurement using an oscillometric method can be executed with one device. As a result, it is highly convenient for the user.

In one aspect, the blood pressure measurement device described above may further comprise a button for initiating blood pressure measurement by the pressing cuff, the fluid supply unit, the pressure sensor, and the second blood pressure value calculation unit, and the third electrode may be provided on the button.

According to the above configuration, it is possible to calculate a feature amount parameter while calibrating a blood pressure calculation formula that represents a correlation between the pulse transit time and blood pressure and to improve the convenience of the user.

Advantageous Effects of Invention

According to the present invention, it is possible to provide a pulse transit time measurement device capable of measuring the pulse transit time more accurately and a blood pressure measurement device using the pulse transit time measurement device.

DESCRIPTION OF EMBODIMENTS

Hereinafter, an embodiment of the present invention will be described with reference to the drawings.

Overview

Figure 1:
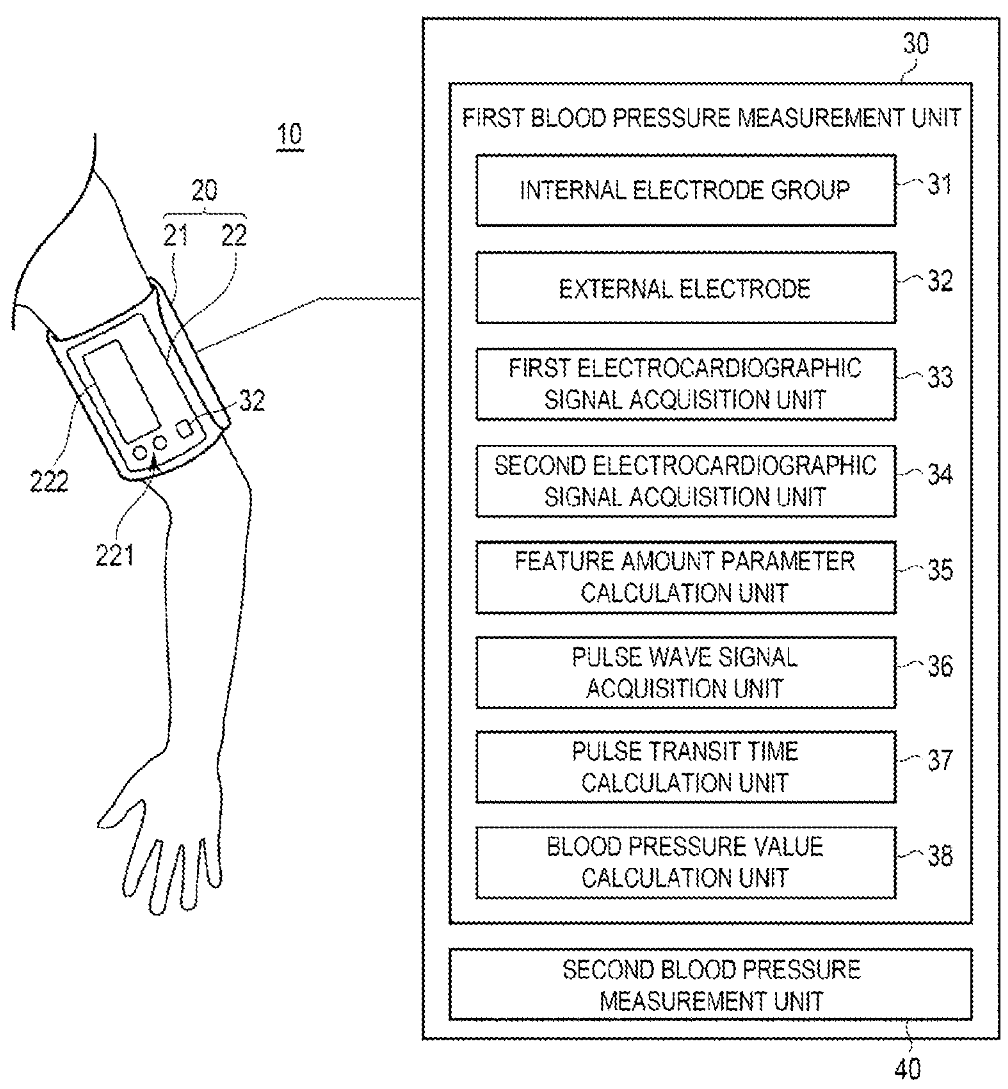
FIG. 1 is a diagram illustrating a blood pressure measurement device according to an embodiment.

FIG. 1 illustrates a blood pressure measurement device 10 according to an embodiment. In the example of FIG. 1, the blood pressure measurement device 10 is a wearable device and is attached to an upper left arm of a user as a target measurement site. The blood pressure measurement device 10 includes a belt unit 20, a first blood pressure measurement unit 30, and a second blood pressure measurement unit 40.

The belt unit 20 has an inner circumferential surface and an outer circumferential surface. The inner circumferential surface is a surface that faces (contacts) the upper left arm of the user in a state in which the blood pressure measurement device 10 is attached to the user (hereinafter, simply referred to as an "attachment state"), and the outer circumferential surface is a surface that does not face (does not contact) the upper left arm of the user in the attachment state. The belt unit 20 includes a belt 21 and a body 22. The belt 21 is a band-like member that is worn around the upper left arm and is sometimes referred to by another name such as a band or a cuff.

The body 22 is mounted on the belt 21. The body 22 accommodates components such as a control unit 501 (illustrated in FIG. 5) described below together with an operation unit 221 and a display unit 222. The operation unit 221 is an input device that allows a user to input an instruction to the blood pressure measurement device 10. In the example of FIG. 1, the operation unit 221 includes a plurality of push buttons. The display unit 222 is a display device displaying information such as a blood pressure measurement result. As a display device, for example, a liquid crystal display (LCD), an organic light emitting diode (OLED) display, and the like can be used. A touch screen that also serves as a display device and an input device may be used.

The first blood pressure measurement unit 30 non-invasively measures a pulse transit time of the user and calculates a blood pressure value based on the measured pulse transit time. The first blood pressure measurement unit 30 can perform continuous blood pressure measurement for obtaining the blood pressure value for each beat. The second blood pressure measurement unit 40 performs blood pressure measurement using a method different from that of the first blood pressure measurement unit 30. The second blood pressure measurement unit 40 is based on, for example, an oscillometric method or a Korotkoff method and performs the blood pressure measurement at a specific timing, for example, in response to operation performed by the user. The second blood pressure measurement unit 40 can measure the blood pressure more accurately than the first blood pressure measurement unit 30.

The first blood pressure measurement unit 30 includes an internal electrode group 31, an external electrode 32, a first electrocardiographic signal acquisition unit 33, a second electrocardiographic signal acquisition unit 34, a feature amount parameter calculation unit 35, a pulse wave signal acquisition unit 36, a pulse transit time calculation unit 37, and a blood pressure value calculation unit 38.

The internal electrode group 31 has a plurality of internal electrodes. These internal electrodes are provided on the inner circumferential surface of the belt unit 20, so that the internal electrodes are in contact with the upper left arm of the user in the attachment state. The internal electrode corresponds to the first electrode of the present invention. In the example described in the present embodiment, the internal electrodes are used by the first electrocardiographic signal acquisition unit 33, and one of the internal electrodes is also used by the second electrocardiographic signal acquisition unit 34. The internal electrode used by the second electrocardiographic signal acquisition unit 34 corresponds to the second electrode of the present invention. The external electrode 32 is provided on the outer circumferential surface of the belt unit 20, so that the external electrode 32 is not in contact with the upper left arm of the user in the attachment state. The external electrode 32 corresponds to the third electrode of the present invention.

The first electrocardiographic signal acquisition unit 33 acquires the user's electrocardiographic signal (ECG signal) using the internal electrode group 31. The electrocardiographic signal is a waveform signal that represents a change over time in the electrical activity of the heart. Specifically, the first electrocardiographic signal acquisition unit 33 acquires the user's electrocardiographic signal on the basis of a potential difference between two internal electrodes selected from the internal electrode group 31. In the following, the electrocardiographic signal obtained by the first electrocardiographic signal acquisition unit 33 is sometimes referred to as a first electrocardiographic signal.

The second electrocardiographic signal acquisition unit 34 acquires the user's electrocardiographic signal using one internal electrode of the internal electrode group 31 and the external electrode 32. Specifically, the second electrocardiographic signal acquisition unit 34 acquires the user's electrocardiographic signal on the basis of a potential difference between one internal electrode and the external electrode 32. The acquisition of the electrocardiographic signal by the second electrocardiographic signal acquisition unit 34 is performed, for example, in a state in which the right hand of the user is in contact with the external electrode 32, that is, using electrodes disposed on the left and right sides of the heart so as to sandwich the heart. This measurement method is a measurement method called the first lead, which is the lead of looking at the side walls of the left ventricle, and is capable of acquiring more accurate electrocardiographic signals. The electrocardiographic signal obtained by the second electrocardiographic signal acquisition unit 34 is sometimes referred to as a second electrocardiographic signal.

The feature amount parameter calculation unit 35 calculates a feature amount parameter related to the waveform feature points of the first electrocardiographic signal, on the basis of the waveform feature points of the second electrocardiographic signal. The waveform feature points may correspond to any of the Q, R, and S-waves. The first electrocardiographic signals acquired using electrodes disposed at a single site (the upper left arm in this example) have a different waveform shape from that of the second electrocardiographic signal that reflects the electrical activity of the heart more accurately. For example, in the first electrocardiographic signal, the amplitude of the waveform feature points is small, and the waveform feature points appear on the positive or negative side depending on the electrode used. Thus, it is difficult to accurately detect a particular waveform feature point in the first electrocardiographic signal. The feature amount parameter calculation unit 35 detects a waveform feature point of the second electrocardiographic signal and determines a time range for detecting the waveform feature point on the basis of the detected waveform feature point. Subsequently, the feature amount parameter calculation unit 35 detects a peak having a maximum amplitude (the absolute value of the amplitude value becomes maximum) in the first electrocardiographic signal acquired simultaneously with the second electrocardiographic signal in the determined time range and acquires the amplitude value of the detected peak as the feature amount parameter.

The pulse wave signal acquisition unit 36 includes a pulse wave sensor and acquires a pulse wave signal representing a pulse wave in the upper left arm of the user, using the pulse wave sensor. The pulse wave sensor is provided on the belt unit 20. For example, the pulse wave sensor is disposed on the inner circumferential surface of the belt unit 20, so that the pulse wave sensor is in contact with the upper left arm of the user in the attachment state. Note that some types of pulse wave sensors, such as pulse wave sensors based on the radio wave method described below, do not need to be in contact with the skin of the user's upper left arm in the attachment state.

The pulse transit time calculation unit 37 is configured to detect a waveform feature point of the first electrocardiographic signal obtained by the first electrocardiographic signal acquisition unit 33 using the feature amount parameter calculated by the feature amount parameter calculation unit 35 and calculate the pulse transit time on the basis of a time difference between the detected waveform feature points of the first electrocardiographic signal and the waveform feature points of the pulse wave signal obtained by the pulse wave signal acquisition unit 36. For example, the pulse transit time calculation unit 37 calculates the time difference between the detected waveform feature point of the first electrocardiographic signal and the waveform feature point of the pulse wave signal as the pulse transit time. In the present embodiment, the timing at which either the Q-wave, the R-wave, or the S-wave of the first electrocardiographic signal peaks is regarded as the drive timing of the heart (for example, the timing at which the heart pumps blood). In the present embodiment, the pulse transit time corresponds to a time required for a pulse wave to propagate through the artery, from the heart to the upper left arm (to be exact, the position where the pulse wave sensor is disposed).

The blood pressure value calculation unit 38 calculates a blood pressure value on the basis of the pulse transit time calculated by the pulse transit time calculation unit 37 and a blood pressure calculation formula. The blood pressure calculation formula is a relational formula that represents a correlation between the pulse transit time and the blood pressure. An example of a blood pressure calculation formula is illustrated below.

$$SBP=A_1/PTT^2+A_2 \quad (1)$$

Here, SBP represents systolic blood pressure, PTT represents the pulse transit time, and $A_1$ and $A_2$ are parameters.

The pulse transit time calculation unit 37 can calculate the pulse transit time for each beat, and thus the blood pressure value calculation unit 38 can calculate the blood pressure value for each beat.

As described above, the blood pressure measurement device 10 calculates a feature amount parameter related to a waveform feature point of the first electrocardiographic signal acquired using the internal electrode group 31, on the basis of the second electrocardiographic signal acquired using one internal electrode of the internal electrode group 31 and the external electrode 32. The use of the feature amount parameter allows the waveform feature point of the first electrocardiographic signal to be detected correctly and allows the pulse transit time to be measured accurately. As a result, the reliability of the blood pressure value calculated on the basis of the pulse transit time is improved.

Hereinafter, the blood pressure measurement device 10 will be described in more detail.

Configuration Example

Hardware Configuration

An example of a hardware configuration of the blood pressure measurement device 10 according to the present embodiment will be described with reference to FIGS. 2 to 6.

Figure 2:
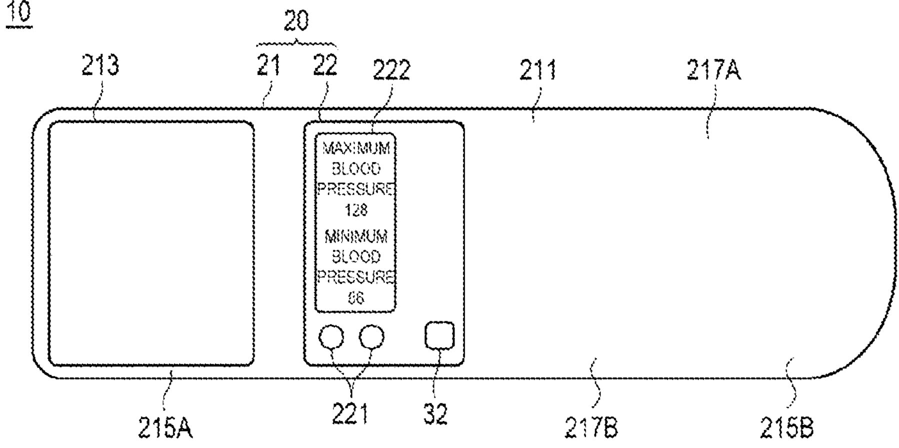
FIG. 2 is a diagram illustrating the appearance of the blood pressure measurement device illustrated in FIG. 1.
Figure 3:
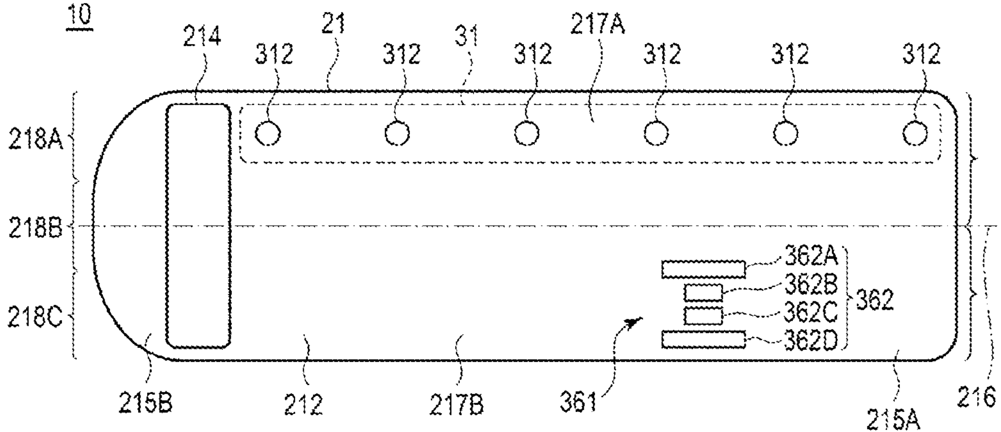
FIG. 3 is a diagram illustrating the appearance of the blood pressure measurement device illustrated in FIG. 1.
Figure 4:
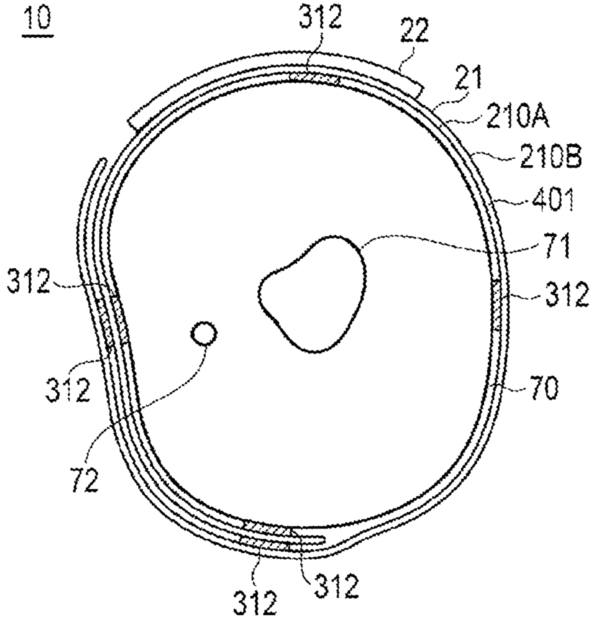
FIG. 4 is a diagram illustrating a cross-section of the blood pressure measurement device illustrated in FIG. 1.

FIGS. 2 and 3 are plan views illustrating the appearance of the blood pressure measurement device 10. Specifically, FIG. 2 illustrates the blood pressure measurement device 10 viewed from an outer circumferential surface 211 of the belt 21 in an expanded state of the belt 21, and FIG. 3 illustrates the blood pressure measurement device 10 viewed from an inner circumferential surface 212 of the belt 21 in an expanded state of the belt 21. FIG. 4 illustrates a cross-section of the blood pressure measurement device 10 in the attachment state.

The belt 21 includes an attachment member allowing the belt 21 to be detachably attached to the upper arm. In the example illustrated in FIGS. 2 and 3, the attachment member is a surface fastener including: a loop surface 213 including a multiplicity of loops; and a hook surface 214 including a plurality of hooks. The loop surface 213 is disposed on the outer circumferential surface 211 of the belt 21 at a longitudinal end portion 215A of the belt 21. The longitudinal direction corresponds to the circumferential direction of the upper arm in the attachment state. The hook surface 214 is disposed on the inner circumferential surface 212 of the belt 21 at a longitudinal end portion 215B of the belt 21. The end portion 215B faces the end portion 215A in the longitudinal direction of the belt 21. When the loop surface 213 and the hook surface 214 are pressed against each other, the loop surface 213 and the hook surface 214 are joined. In addition, pulling the loop surface 213 and the hook surface 214 away from each other separates the loop surface 213 and the hook surface 214.

As illustrated in FIG. 3, the internal electrode group 31 is disposed on the inner circumferential surface 212 of the belt 21. In the example of FIG. 3, the internal electrode group 31 has six internal electrodes 312 aligned at regular intervals in the longitudinal direction of the belt 21. The interval between the internal electrodes 312 is set, for example, to a quarter of the circumference of the upper arm of the user expected to have the thinnest arm. In this arrangement, as illustrated in FIG. 4, for a user expected to have the thinnest arm, four of the six internal electrodes 312 contact the upper left arm 70 in the attachment state and are positioned at regular intervals on the circumference of the upper left arm 70, and the remaining two internal electrodes 312 contact the outer circumferential surface 211 of the belt 21. In FIG. 4, a humerus 71 and a brachial artery 72 are illustrated. For a user expected to have the thickest arm, all the six internal electrodes 312 contact the upper left arm 70 in the attachment state.

Note that the number of internal electrodes 312 is not limited to six, and may be two to five or seven or greater. If two or three internal electrodes 312 are in contact with the upper left arm, the first electrocardiographic signal may not be successfully measured depending on the attachment state. If the first electrocardiographic signal is not successfully measured, a message may be displayed on the display unit 222, and the blood pressure measurement device 10 needs to be re-attached to the user. In order to avoid situations in which the first electrocardiographic signal cannot be measured, it is desired that at least four internal electrodes 312 contact the upper left arm in the attachment state.

The closer the internal electrode 312 is to the heart in the attachment state, the greater the signal representing the electrical activity of the heart and acquired using the internal electrode 312 becomes, that is, the signal to noise ratio (SN ratio) becomes higher. Preferably, as illustrated in FIG. 3, the internal electrodes 312 are disposed in a central side portion 217A of the belt 21. The central side portion 217A is a portion that is located closer to the central side (the shoulder side) than a center line 216 in the attachment state. More preferably, the internal electrode 312 is disposed at a central end portion 218A of the belt 21. The central end portion 218A is an end portion located on the central side in the attachment state, and the width of the central end portion 218A is, for example, one-third of the full width of the belt 21.

As illustrated in FIG. 2, the external electrode 32 is provided on the body 22. Note that the external electrode 32 may be provided on the outer circumferential surface 211 of the belt 21.

A sensor unit 362 of an impedance measurement unit 361 is further disposed on the inner circumferential surface 212 of the belt 21. In the example of FIG. 3, the sensor unit 362 includes a pair of electrodes 362A, 362D for energizing the upper left arm and a pair of electrodes 362B, 362C for detecting a voltage. The pair of electrodes 362B, 362C form the pulse wave sensor. The electrodes 362A, 362B, 362C, 362D are arranged in that order in the width direction of the belt 21. The width direction of the belt 21 corresponds to a direction along the brachial artery 72 in the attachment state.

The farther the sensor unit 362 is located from the heart in the attachment state, the longer the pulse transit distance is and the greater the measurement value of the pulse transit time is. If the measurement value of the pulse transit time is large, the error generated in calculating the time difference between the waveform feature point of the first electrocardiographic signal and the waveform feature point of the pulse wave signal is relatively smaller than the pulse transit time, and the pulse transit time can be accurately measured. Thus, preferably, the sensor unit 362 is disposed in a peripheral side portion 217B of the belt 21. The peripheral side portion 217B is a portion that is positioned closer to the peripheral side (the elbow side) than the center line 216 in the attachment state. More preferably, the sensor unit 362 is disposed at a peripheral end portion 218C of the belt 21. The peripheral end portion 218C is an end portion located on the peripheral side in the attachment state, and the width of the peripheral end portion 218C is, for example, one-third the full width of the belt 21. A portion 218B between the central end portion 218A and the peripheral end portion 218C is referred to as an intermediate portion.

As illustrated in FIG. 4, the belt 21 includes an inner cloth 210A an outer cloth 210B, and a pressing cuff 401 is provided between the inner cloth 210A and the outer cloth 210B. The pressing cuff 401 is a band-like member that is long in the longitudinal direction of the belt 21 such that the pressing cuff 401 can surround the upper left arm. For example, the pressing cuff 401 is configured as a fluid bag by placing two stretchable polyurethane sheets opposite each other in the thickness direction and welding the edge portions of the polyurethane sheets. The internal electrode group 31 and the sensor unit 362 are provided in the inner cloth 210A such that the internal electrode group 31 and the sensor unit 362 are positioned between the pressing cuff 401 and the upper left arm 70 in the attachment state.

Figure 5:
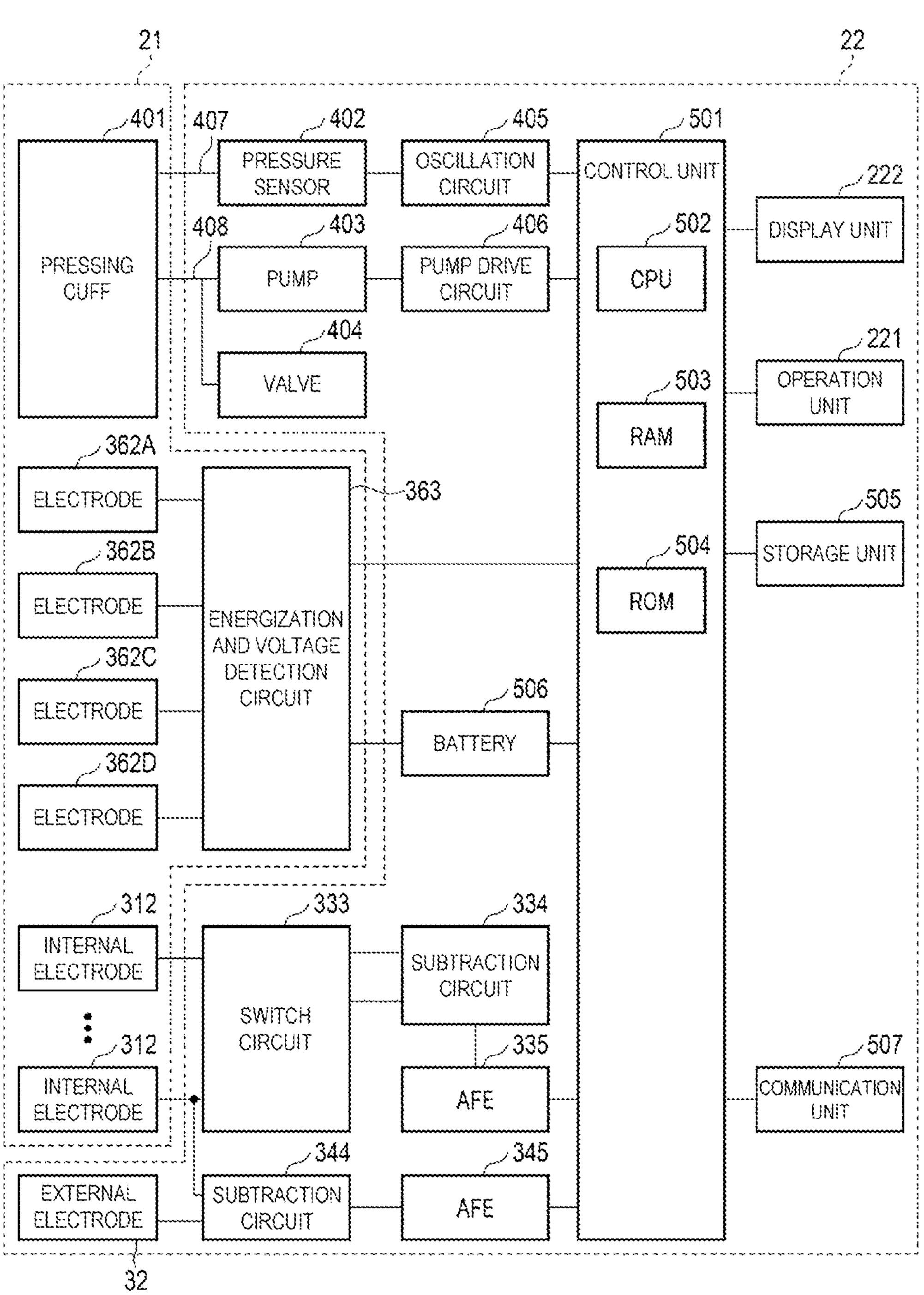
FIG. 5 is a block diagram illustrating a hardware configuration of a control system of the blood pressure measurement device illustrated in FIG. 1.

FIG. 5 illustrates an example of a hardware configuration of a control system of the blood pressure measurement device 10 according to the present embodiment. In the example of FIG. 5, in addition to the operation unit 221 and the display unit 222 described above, the body 22 includes the control unit 501, a storage unit 505, a battery 506, a switch circuit 333, a subtraction circuit 334, an analog front end (AFE) 335, a subtraction circuit 344, an AFE 345, a pressure sensor 402, a pump 403 as a fluid supply unit, a valve 404, an oscillation circuit 405, and a pump drive circuit 406. The body 22 may be provided with a sound emitter such as a speaker or a piezoelectric sounder. The body 22 may be provided with a microphone to allow the user to input instructions by sounds. In addition to the sensor unit 362 described above, the impedance measurement unit 361 includes an energization and voltage detection circuit 363. In this example, the energization and voltage detection circuit 363 is provided on the belt 21.

The control unit 501 includes a Central Processing Unit (CPU) 502, a Random Access Memory (RAM) 503, a Read Only Memory (ROM) 504, and the like and controls each component according to information processing. The storage unit 505 is an auxiliary storage device such as, for example, a hard disk drive (HDD) or a semiconductor memory (for example, a flash memory) and non-transitorily stores: programs executed by the control unit 501 (including, for example, a pulse transit time measurement program and a blood pressure measurement program), settings data necessary for executing the programs, the blood pressure measurement result, and the like. A storage medium included in the storage unit 505 is, to enable computers, other devices, machines, or the like to read information such as recorded programs, a medium that stores information such as the programs, by using electrical, magnetic, optical, mechanical, or chemical actions. Note that some or all of the programs may be stored in the ROM 504.

The battery 506 supplies electric power to components such as the control unit 501. The battery 506 is, for example, a rechargeable battery.

The six internal electrodes 312 are connected to an input terminal of the switch circuit 333. The two output terminals of the switch circuit 333 are connected to two input terminals of the subtraction circuit 334. The switch circuit 333 receives a switch signal from the control unit 501 and connects the two internal electrodes 312 designated by the switch signal to the subtraction circuit 334. The subtraction circuit 334 subtracts, from the potential input from one input terminal, the potential input from the other input terminal. The subtraction circuit 334 outputs, to the AFE 335, a potential difference signal that represents the potential difference between the two interconnected internal electrodes 312. The subtraction circuit 334 is, for example, an instrumentation amplifier. AFE 335 includes, for example, a low-pass filter (LPF), an amplifier, and an analog-to-digital converter. The potential difference signal is filtered by the LPF, amplified by the amplifier, and converted to a digital signal by the analog-to-digital converter. The potential difference signal converted to the digital signal is provided to the control unit 501. The control unit 501 acquires, from the AFE 335, the potential difference signal output in a time-series manner as the first electrocardiographic signal.

One of the six internal electrodes 312 is further connected to one input terminal of the subtraction circuit 344. The external electrode 32 is connected to the other input terminal of the subtraction circuit 344. The subtraction circuit 344 outputs, to the AFE 345, a potential difference signal representing the potential difference between the internal electrode 312 and the external electrode 32. The subtraction circuit 344 is, for example, an instrumentation amplifier. The AFE 345 includes, for example, an LPF, an amplifier, and an analog-to-digital converter. The potential difference signal is filtered by the LPF, amplified by the amplifier, and converted to a digital signal by the analog-to-digital converter. The potential difference signal converted to the digital signal is provided to the control unit 501. The control unit 501 acquires, from the AFE 345, the potential difference signal output in a time-series manner as the second electrocardiographic signal.

The energization and voltage detection circuit 363 allows a high-frequency constant current to flow between the electrodes 362A, 362D. In this example, the current has a frequency of 50 kHz and a current value of 1 mA. The energization and voltage detection circuit 363 detects the voltage across the electrodes 362B, 362C and generates a detection signal, in a state in which a current flows between the electrodes 362A, 362D. The detection signal represents a change in electrical impedance due to a pulse wave that propagates through a portion of the artery that faces the electrodes 362B, 362C. The energization and voltage detection circuit 363 performs signal processing including rectifying, amplifying, filtering, and analog-to-digital conversion on the detection signal and supplies the detection signal to the control unit 501. The control unit 501 acquires, from the energization and voltage detection circuit 363, the detection signal output in a time-series manner as a pulse wave signal.

The pressure sensor 402 is connected to the pressing cuff 401 via a pipe 407, and the pump 403 and the valve 404 are connected to the pressing cuff 401 via a pipe 408. The pipes 407, 408 may be a single common pipe. The pump 403 is, for example, a piezoelectric pump and feeds air as a fluid to the pressing cuff 401 through the pipe 408 in order to increase the pressure inside the pressing cuff 401. The valve 404 is mounted on the pump 403, and opening and closing of the valve 404 is controlled according to an operation state (on/off) of the pump 403. Specifically, the valve 404 is in a closed state when the pump 403 is turned on, and the valve 404 is in an open state when the pump 403 is turned off. When the valve 404 is in an open state, the pressing cuff 401 is in communication with the atmosphere, and air in the pressing cuff 401 is discharged into the atmosphere. The valve 404 has a function of a check valve, and air does not flow back through it. The pump drive circuit 406 drives the pump 403 on the basis of a control signal received from the control unit 501.

The pressure sensor 402 detects the pressure in the pressing cuff 401 (also referred to as cuff pressure) and generates an electric signal representing the cuff pressure. The cuff pressure is, for example, pressure based on the atmospheric pressure as a reference. The pressure sensor 402 is, for example, a piezoresistive pressure sensor. The oscillation circuit 405 oscillates on the basis of the electric signal from the pressure sensor 402 and outputs, to the control unit 501, a frequency signal having a frequency corresponding to the electric signal. In this example, the output of the pressure sensor 402 is used for controlling the pressure of the pressing cuff 401 and for calculating a blood pressure value (including a systolic blood pressure and a diastolic blood pressure) using an oscillometric method.

The pressing cuff 401 may be used for adjusting the contact state between the upper left arm and the internal electrode 312 or the sensor unit 362 of the impedance measurement unit 361. For example, during execution of the blood pressure measurement based on the pulse transit time, the pressing cuff 401 is maintained in a state in which some air is accommodated therein. As a result, the internal electrode 312 and the sensor unit 362 of the impedance measurement unit 361 are reliably in contact with the upper left arm of the user.

In the example illustrated in FIGS. 2 to 5, the switch circuit 333, the subtraction circuit 334, and the AFE 335 are included in the first electrocardiographic signal acquisition unit 33 illustrated in FIG. 1, the subtraction circuit 344 and the AFE 345 are included in the second electrocardiographic signal acquisition unit 34 illustrated in FIG. 1, and the impedance measurement unit 361 (including the electrodes 362A to 362D and the energization and voltage detection circuit 363) is included in the pulse wave signal acquisition unit 36 illustrated in FIG. 1. Also, the pressing cuff 401, the pressure sensor 402, the pump 403, the valve 404, the oscillation circuit 405, the pump drive circuit 406, and the pipes 407, 408 are included in the second blood pressure measurement unit 40 illustrated in FIG. 1.

Also, with respect to a specific hardware configuration of the blood pressure measurement device 10, components can be omitted, replaced, or added as appropriate in accordance with embodiments. For example, the control unit 501 may include a plurality of processors. The blood pressure measurement device 10 may include a communication unit 507 for communicating with an external device such as a portable terminal of the user (for example, a smartphone). The communication unit 507 includes a wired communication module and/or a wireless communication module. As a wireless system, for example, Bluetooth (trade name), Bluetooth Low Energy (BLE), or the like can be adopted.

Software Configuration

Figure 6:
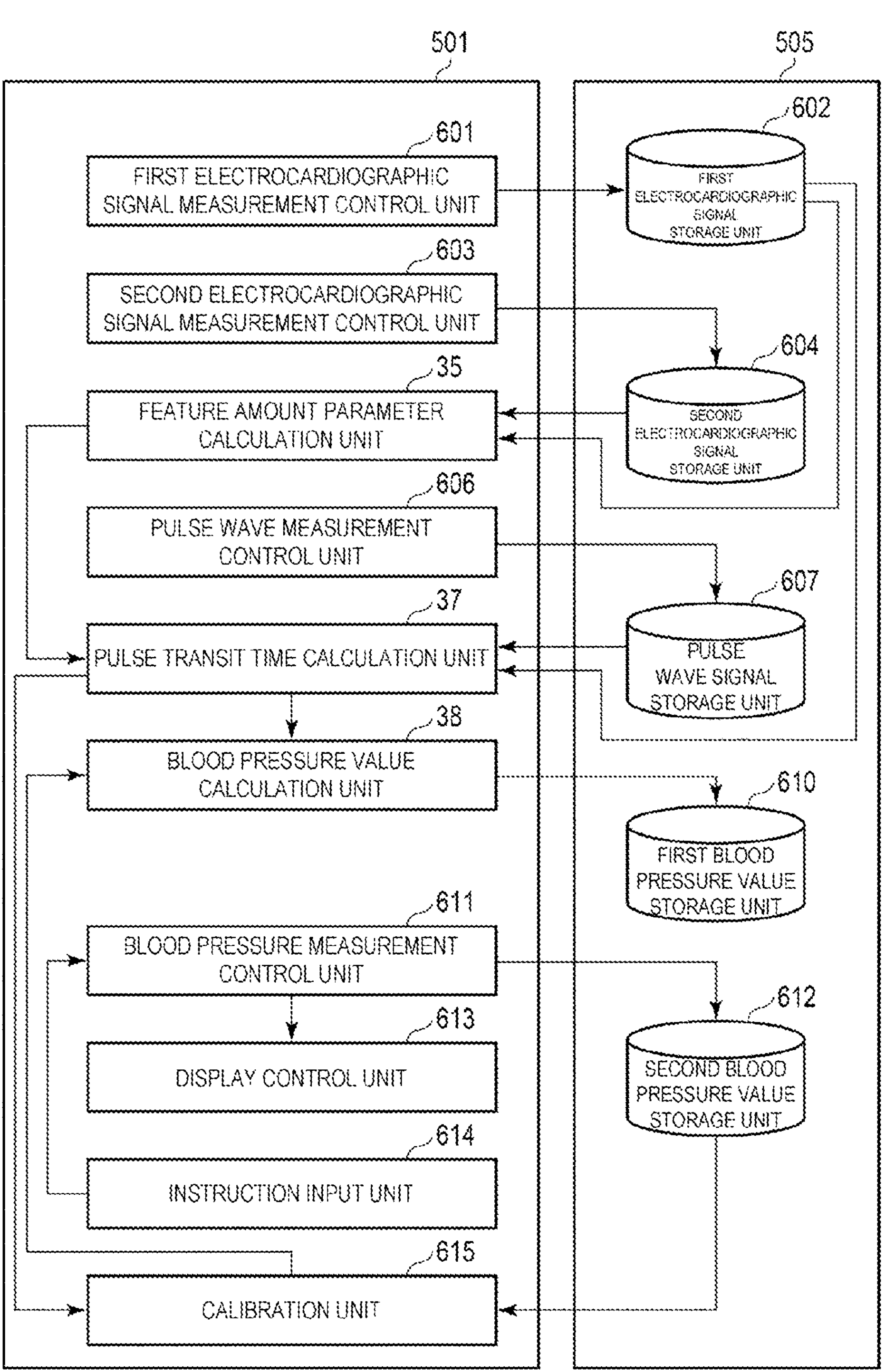
FIG. 6 is a block diagram illustrating a software configuration of the blood pressure measurement device illustrated in FIG. 1.

An example of a software configuration of the blood pressure measurement device 10 according to the present embodiment will be described with reference to FIG. 6. FIG. 6 illustrates one example of the software configuration of the blood pressure measurement device 10. In the example of FIG. 6, the blood pressure measurement device 10 includes a first electrocardiographic signal measurement control unit 601, a first electrocardiographic signal storage unit 602, a second electrocardiographic signal measurement control unit 603, a second electrocardiographic signal storage unit 604, the feature amount parameter calculation unit 35, a pulse wave measurement control unit 606, a pulse wave signal storage unit 607, the pulse transit time calculation unit 37, the blood pressure value calculation unit 38, a first blood pressure value storage unit 610, a blood pressure measurement control unit 611, a second blood pressure value storage unit 612, a display control unit 613, an instruction input unit 614, and a calibration unit 615. The first electrocardiographic signal measurement control unit 601, the second electrocardiographic signal measurement control unit 603, the feature amount parameter calculation unit 35, the pulse wave measurement control unit 606, the pulse transit time calculation unit 37, the blood pressure value calculation unit 38, the blood pressure measurement control unit 611, the display control unit 613, the instruction input unit 614, and the calibration unit 615 execute the following processing when the control unit 501 of the blood pressure measurement device 10 executes the programs stored in the storage unit 505. When the control unit 501 executes the program, the control unit 501 loads the program in the RAM 503. Then, the control unit 501 causes the CPU 502 to interpret and execute the program loaded in the RAM 503 to control each component. The first electrocardiographic signal storage unit 602, the second electrocardiographic signal storage unit 604, the pulse wave signal storage unit 607, the first blood pressure value storage unit 610, and the second blood pressure value storage unit 612 are implemented by the storage unit 505.

The first electrocardiographic signal measurement control unit 601 controls the switch circuit 333 to acquire the first electrocardiographic signal. Specifically, the first electrocardiographic signal measurement control unit 601 generates a switch signal for selecting two internal electrodes 312 from among the six internal electrodes 312 and provides the switch signal to the switch circuit 333. The first electrocardiographic signal measurement control unit 601 acquires the potential difference signal acquired using the two selected internal electrodes 312 and stores the time-series data of the acquired potential difference signal in the first electrocardiographic signal storage unit 602 as the first electrocardiographic signal.

The first electrocardiographic signal measurement control unit 601 operates as an electrode selection unit to determine an internal electrode pair optimal for acquiring electrocardiographic signals. The selection of the electrode pair is executed, for example, when the blood pressure measurement device 10 is attached to the upper left arm of the user. For example, the first electrocardiographic signal measurement control unit 601 acquires an electrocardiographic signal for each possible pair of internal electrodes and determines an internal electrode pair that provides an electrocardiographic signal with the greatest amplitude of the R-wave as the optimal electrode pair. Thereafter, the first electrocardiographic signal measurement control unit 601 acquires the first electrocardiographic signal using the optimal internal electrode pair.

The second electrocardiographic signal measurement control unit 603 acquires a potential difference signal acquired using one internal electrode 312 and the external electrode 32 and stores the time-series data of the acquired potential difference signal in the second electrocardiographic signal storage unit 604 as a second electrocardiographic signal. The second electrocardiographic signal is acquired in synchronization with the first electrocardiographic signal to calculate the feature amount parameter. At least a portion of the period in which the first electrocardiographic signal is measured may overlap at least a portion of the period in which the second electrocardiographic signal is measured.

The feature amount parameter calculation unit 35 reads the second electrocardiographic signal from the second electrocardiographic signal storage unit 604, detects a waveform feature point of the second electrocardiographic signal, and determines a time range centered on the detected waveform feature points. The feature amount parameter calculation unit 35 reads the first electrocardiographic signal acquired in synchronization with the second electrocardiographic signal from the first electrocardiographic signal storage unit 602, detects a peak point with the maximum amplitude of the first electrocardiographic signal in the determined time range, and calculates the amplitude value of the detected peak point as the feature amount parameter. Note that the feature amount parameter is not limited to the amplitude value of the detected peak point and may be the sign (positive or negative) of the amplitude value of the detected peak point.

Figure 7:
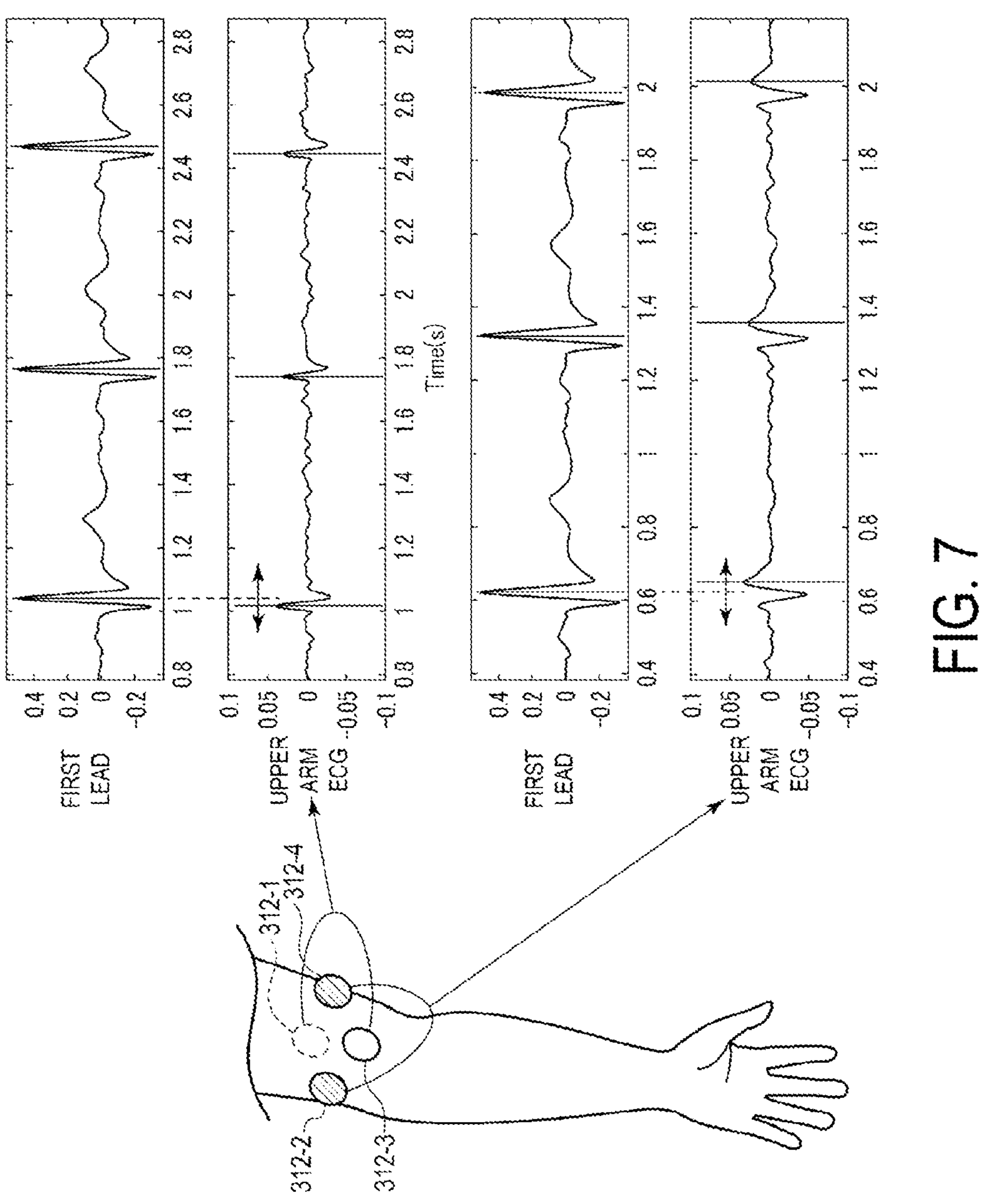
FIG. 7 is a diagram illustrating an example of a method in which a feature amount parameter calculation unit illustrated in FIG. 6 calculates a feature amount parameter.

Referring to FIG. 7, an example of a method of calculating the feature amount parameter will be described. In FIG. 7, four internal electrodes 312 are illustrated and designated as internal electrodes 312-1, 312-2, 312-3, and 312-4 to distinguish between these four internal electrodes 312. The second-stage graph is the first electrocardiographic signal acquired using the internal electrodes 312-1, 312-3, and the first-stage graph is the second electrocardiographic signal acquired simultaneously with the first electrocardiographic signal on the second stage. The fourth-stage graph is the first electrocardiographic signal acquired using the internal electrodes 312-2, 312-4, and the third-stage graph is the second electrocardiographic signal acquired simultaneously with the first electrocardiographic signal on the fourth stage. As illustrated in FIG. 7, the first electrocardiographic signal acquired with the internal electrode pair 312-1, 312-3 has a different waveform shape from that of the first electrocardiographic signal acquired using the internal electrode pair 312-2, 312-4. In the first electrocardiographic signal acquired using the internal electrode pair 312-1, 312-3, the R-wave peak point has a positive amplitude value. In contrast, in the first electrocardiographic signal acquired with the internal electrode pair 312-2, 312-4, the R-wave peak point has a negative amplitude value.

The feature amount parameter calculation unit 35 detects the R-wave peak point of the second electrocardiographic signal and determines a time range (indicated as a double-sided arrow in FIG. 7) centered on the time of the detected R-wave peak point. Then, the feature amount parameter calculation unit 35 detects, in the determined time range, a peak point with the maximum amplitude of the first electrocardiographic signal and acquires the amplitude value of the detected peak point as the feature amount parameter.

Note that the feature amount parameter calculation unit 35 may calculate the feature amount parameter related to a peak point corresponding to a Q-wave or an S-wave without being limited to the R-wave. Since the R-wave appears more clearly than the Q-wave or the S-wave, the peak point corresponding to the R-wave can be identified more accurately than the peak point corresponding to the Q-wave or the S-wave. Therefore, preferably, the feature amount parameter calculation unit 35 calculates the feature amount parameter for the R-wave peak point.

Referring again to FIG. 6, the pulse wave measurement control unit 606 controls energization and voltage detection circuit 363 to acquire the pulse wave signal. Specifically, the pulse wave measurement control unit 606 instructs the energization and voltage detection circuit 363 to flow a current between the electrodes 362A, 362D and acquires a detection signal indicating the voltage between the electrodes 362B, 362C detected with the current flowing between the electrodes 362A, 362D. The pulse wave measurement control unit 606 stores the time-series data of the detection signal in the pulse wave signal storage unit 607 as a pulse wave signal.

Figure 8:
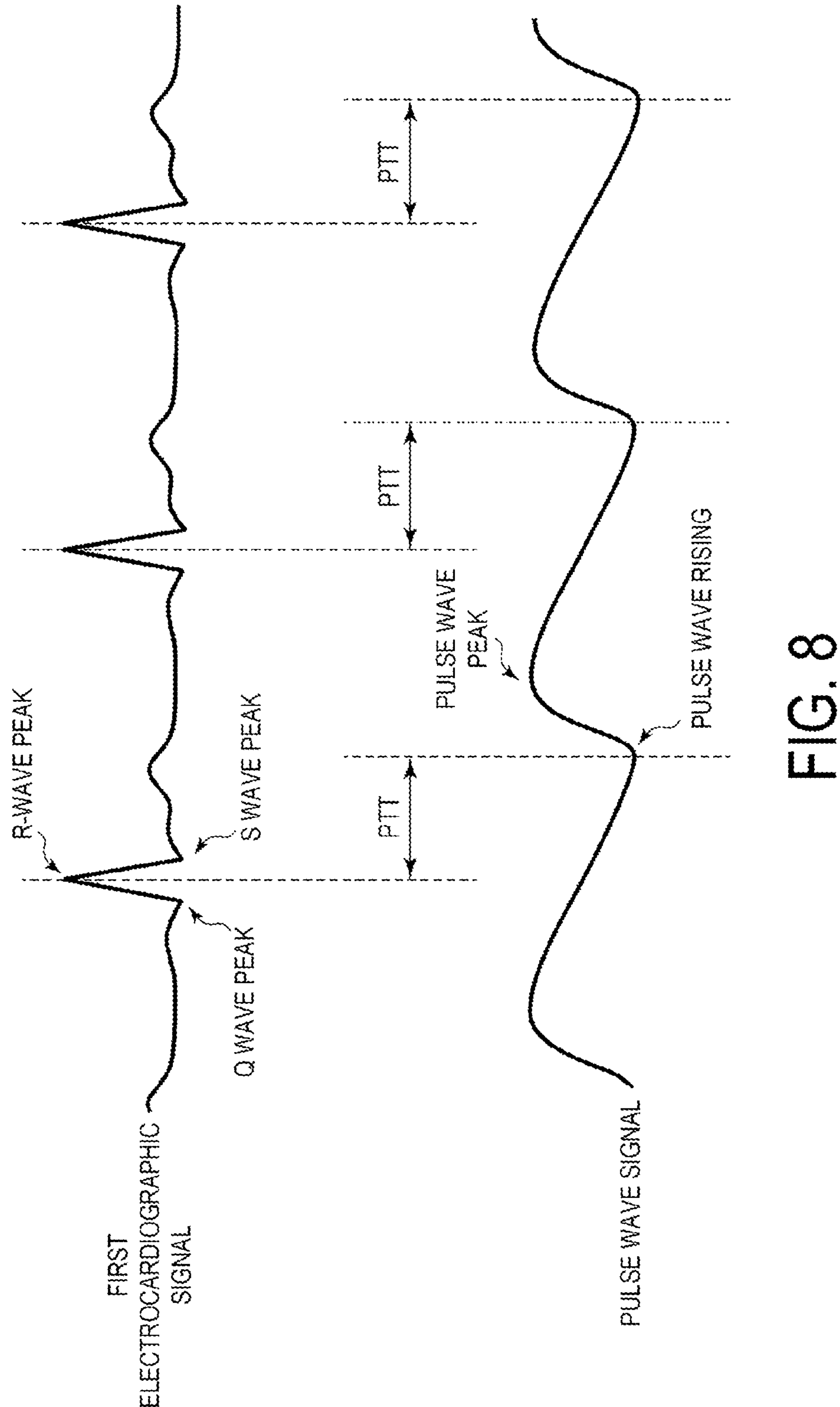
FIG. 8 is a diagram illustrating an example of a method in which a pulse transit time calculation unit illustrated in FIG. 6 calculates a pulse transit time.

The pulse transit time calculation unit 37 reads the first electrocardiographic signal acquired using the optimal internal electrode pair from the first electrocardiographic signal storage unit 602, reads the pulse wave signal from the pulse wave signal storage unit 607, and receives the feature amount parameter from the feature amount parameter calculation unit 35. The pulse transit time calculation unit 37 detects the R-wave peak point of the first electrocardiographic signal with reference to the feature amount parameter and calculates a pulse transit time on the basis of a time difference between the detected R-wave peak point of the first electrocardiographic signal and the rising point of the pulse wave signal. The pulse transit time calculation unit 37 can identify an amplitude value that the R-wave peak point can take on the basis of the feature amount parameter and thus can correctly detect the R-wave peak point of the first electrocardiographic signal. For example, when detecting the R-wave peak point, the S-wave peak point will not be detected erroneously. For example, as illustrated in FIG. 8, the pulse transit time calculation unit 37 detects the time of the R-wave peak point from the first electrocardiographic signal, detects the time of the rising point from the pulse wave signal, and calculates a time difference obtained by subtracting the time of the R-wave peak point from the time of the rising point as the pulse transit time.

The peak point corresponding to the R-wave is an example of a waveform feature point of an electrocardiographic signal. The waveform feature point of the electrocardiographic signal may be a peak point corresponding to the Q-wave or a peak point corresponding to the S-wave. Since the R-wave appears with a clearer peak than the Q-wave or the S-wave, the time of the R-wave peak point can be identified more accurately. Thus, preferably, the R-wave peak point is used as the waveform feature point of the electrocardiographic signal. Additionally, the rising point is an example of a waveform feature point in the pulse wave signal. The waveform feature point in the pulse wave signal may be the peak point.

The blood pressure value calculation unit 38 calculates a blood pressure value on the basis of the pulse transit time calculated by the pulse transit time calculation unit 37 and a blood pressure calculation formula. The blood pressure value calculation unit 38 uses Formula (1) above as a blood pressure calculation formula, for example. The blood pressure value calculation unit 38 stores the calculated blood pressure value in the first blood pressure value storage unit 610 in association with time information.

Note that the blood pressure calculation formula is not limited to Formula (1) above. The blood pressure calculation formula may be, for example, the following formula.

$$SBP=B_1/PTT^2+B_2/PTT+B_3\times PTT+B_4 \quad (2)$$

Here, $B_1$, $B_2$, $B_3$, and $B_4$ are parameters.

The blood pressure measurement control unit 611 controls the pump drive circuit 406 to execute the blood pressure measurement using the oscillometric method. Specifically, the blood pressure measurement control unit 611 drives the pump 403 via the pump drive circuit 406. In this way, supply of air to the pressing cuff 401 starts. The pressing cuff 401 is inflated, whereby the upper left arm of the user is compressed. The blood pressure measurement control unit 611 monitors the cuff pressure using the pressure sensor 402. The blood pressure measurement control unit 611 calculates the blood pressure value using the oscillometric method on the basis of a pressure signal output from the pressure sensor 402 in the pressurizing process of supplying air to the pressing cuff 401. Although the blood pressure value includes the systolic blood pressure (SBP) and the diastolic blood pressure (DBP), it is not limited thereto. The blood pressure measurement control unit 611 stores the calculated blood pressure value in the second blood pressure value storage unit 612 in association with time information. The blood pressure measurement control unit 611 can calculate a pulse rate at the same time as the blood pressure value. The blood pressure measurement control unit 611 stops the pump 403 via the pump drive circuit 406 when calculation of the blood pressure value is completed. Thus, air is exhausted from the pressing cuff 401 through the valve 404.

The display control unit 613 controls the display unit 222. For example, the display control unit 613 displays the blood pressure measurement result on the display unit 222 after the blood pressure measurement by the blood pressure measurement control unit 611 has been completed.

The instruction input unit 614 receives an instruction input from the user through the operation unit 221. For example, when operation instructing execution of blood pressure measurement is performed, the instruction input unit 614 provides the blood pressure measurement control unit 611 with an initiation instruction of the blood pressure measurement. The blood pressure measurement control unit 611 starts the blood pressure measurement upon receiving an initiation instruction of blood pressure measurement from the instruction input unit 614.

The calibration unit 615 calibrates the blood pressure calculation formula on the basis of the pulse transit time obtained by the pulse transit time calculation unit 37 and the blood pressure value obtained by the blood pressure measurement control unit 611. The correlation between the pulse transit time and blood pressure values varies from individual to individual. Additionally, the correlation also varies depending on the state in which the blood pressure measurement device 10 is attached to the upper left arm of the user. For example, even within an identical user, the correlation varies between positioning of the blood pressure measurement device 10 closer to the shoulder and positioning of the blood pressure measurement device 10 closer to the elbow. To reflect such a variation in correlation, the blood pressure calculation formula is calibrated. The calibration of the blood pressure calculation formula is performed, for example, when the blood pressure measurement device 10 is attached to the user. The calibration unit 615 acquires a plurality of sets of measurement result for the pulse transit time and measurement result for the blood pressure to determine parameters A1 and A2, on the basis of the plurality of sets of the measurement result for the pulse transit time and the measurement result for the blood pressure. In order to determine the parameters A1 and A2, the calibration unit 615 uses a fitting method such as, for example, a least squares method or a maximum likelihood method.

Also, the present embodiment describes an example in which all the functions of the blood pressure measurement device 10 are realized by a general-purpose processor. However, some or all of the functions may be implemented by one or more dedicated processors.

Operation Example

Selection of Internal Electrode Pair Used for Acquiring First Electrocardiographic Signal When the blood pressure measurement device 10 is attached to the user, first, a process of selecting an optimal internal electrode pair to acquire the first electrocardiographic signal is executed. In this process, the control unit 501 operates as the first electrocardiographic signal measurement control unit 601. In this example, it is assumed that the internal electrode group 31 includes four internal electrodes 312, and the internal electrodes are designated as the internal electrodes 312-1, 312-2, 312-3, 312-4 to distinguish between these four internal electrodes 312. The control unit 501 provides a switch signal for selecting the internal electrodes 312-1, 312-2 to the switch circuit 333 and acquires the first electrocardiographic signal using the pair of internal electrodes 312-1, 312-2. Subsequently, the control unit 501 provides a switch signal for selecting the internal electrodes 312-1, 312-3 to the switch circuit 333 and acquires the first electrocardiographic signal using the pair of internal electrodes 312-1, 312-3. Similarly, the control unit 501 acquires the first electrocardiographic signal using the pair of internal electrodes 312-1, 312-4, the pair of internal electrodes 312-2, 312-3, the pair of internal electrodes 312-2, 312-4, and the pair of internal electrodes 312-3, 312-4. The control unit 501 determines an internal electrode pair that provides the first electrocardiographic signal having the greatest R-wave amplitude as an optimal internal electrode pair.

Calculation of Feature Amount Parameter

Figure 9:
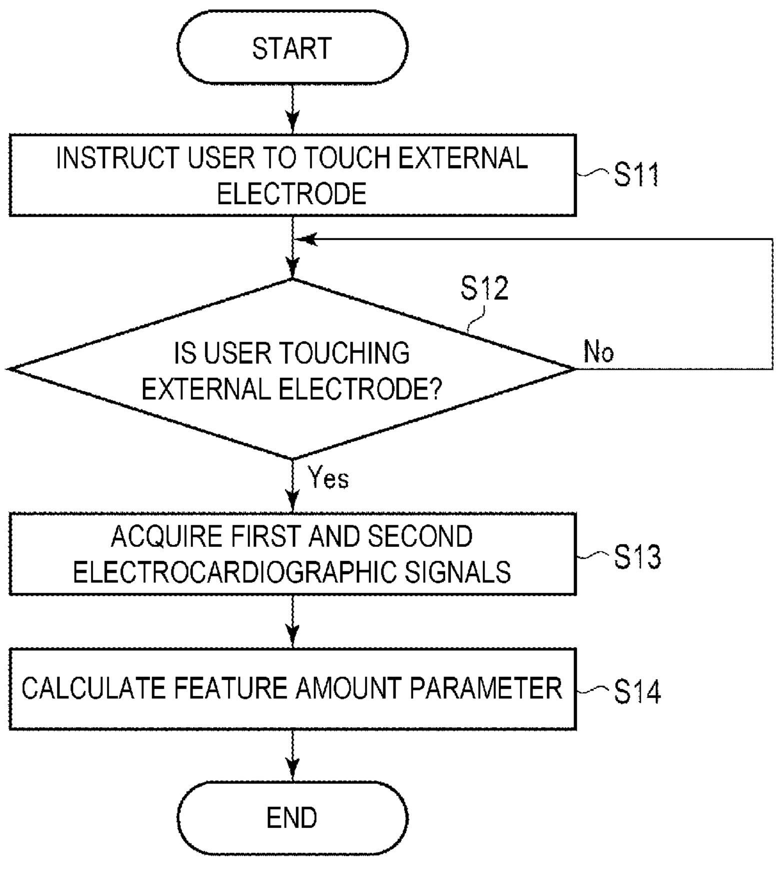
FIG. 9 is a flowchart illustrating operation in which the blood pressure measurement device illustrated in FIG. 1 calculates a feature amount parameter.

FIG. 9 illustrates an operation flow when the blood pressure measurement device 10 calculates the feature amount parameter. The control unit 501 starts calculating the feature amount parameter immediately after the above-described selection process is completed, for example. Moreover, the control unit 501 may calculate the feature amount parameter before starting the blood pressure measurement based on the pulse transit time in response to receiving an operation signal from the operation unit 221 indicating that the user has instructed to start blood pressure measurement based on the pulse transit time. That is, the process illustrated in FIG. 9 may be executed between steps S21 and S22 of FIG. 10.

In step S11 of FIG. 9, the control unit 501 instructs the user to touch the external electrode 32 with the right hand. Here, the blood pressure measurement device 10 is attached to the upper left arm of the user. For example, the control unit 501 displays a message "Please touch the electrodes on the body with the index finger of the right hand" on the display unit 222. The message may be output as sound through a speaker.

In step S12, the control unit 501 determines whether the user is touching the external electrode 32. The determination of whether the user is touching the external electrode 32 can be made, for example, on the basis of the output of the AFE 345. Upon detecting that the user is touching the external electrode 32, the control unit 501 proceeds to step S13.

In step S13, the control unit 501 acquires the first electrocardiographic signal and the second electrocardiographic signal at the same time. For example, the control unit 501 operates as the first electrocardiographic signal measurement control unit 601 and acquires the first electrocardiographic signal using the optimal internal electrode pair. Furthermore, the control unit 501 operates as the second electrocardiographic signal measurement control unit 603 and acquires the second electrocardiographic signal using the internal electrode 312 and the external electrode 32.

In step S14, the control unit 501 operates as the feature amount parameter calculation unit 35 and calculates the feature amount parameter for the R-wave peak point of the first electrocardiographic signal on the basis of the second electrocardiographic signal. For example, the control unit 501 detects the R-wave peak point of the second electrocardiographic signal, determines a time range on the basis of the detected R-wave peak point, detects a peak point in the first electrocardiographic signal in the determined time range, and calculates an amplitude value of the detected peak point as a feature amount parameter.

Calibration of Blood Pressure Calculation Formula Used in Blood Pressure Measurement Based on Pulse Transit Time Subsequently, calibration of the blood pressure calculation formula is executed. Assuming that N is the number of the parameters included in the blood pressure calculation formula, N or more sets of a measurement value for the pulse transit time and a measurement value for the blood pressure are required. The blood pressure calculation Formula (1) described above includes two parameters $A_1$ and $A_2$. In this case, for example, the control unit 501 acquires a set of measurement value for the pulse transit time and measurement value for the blood pressure when the user is at rest. The control unit 501 acquires the set of the measurement value for the pulse transit time and the measurement value for the blood pressure after varying the user's blood pressure, such as by causing the user to exercise. Thus, two sets of the measurement value for the pulse transit time and the measurement value for the blood pressure are acquired. The control unit 501 operates as the calibration unit 615 and determines the parameters A1 and A2 on the basis of the acquired two sets of the measurement value for the pulse transit time and the measurement value for the blood pressure. After the calibration of the blood pressure calculation formula is completed, blood pressure measurement based on the pulse transit time can be executed.

Blood Pressure Measurement Based on Pulse Transit Time

Figure 10:
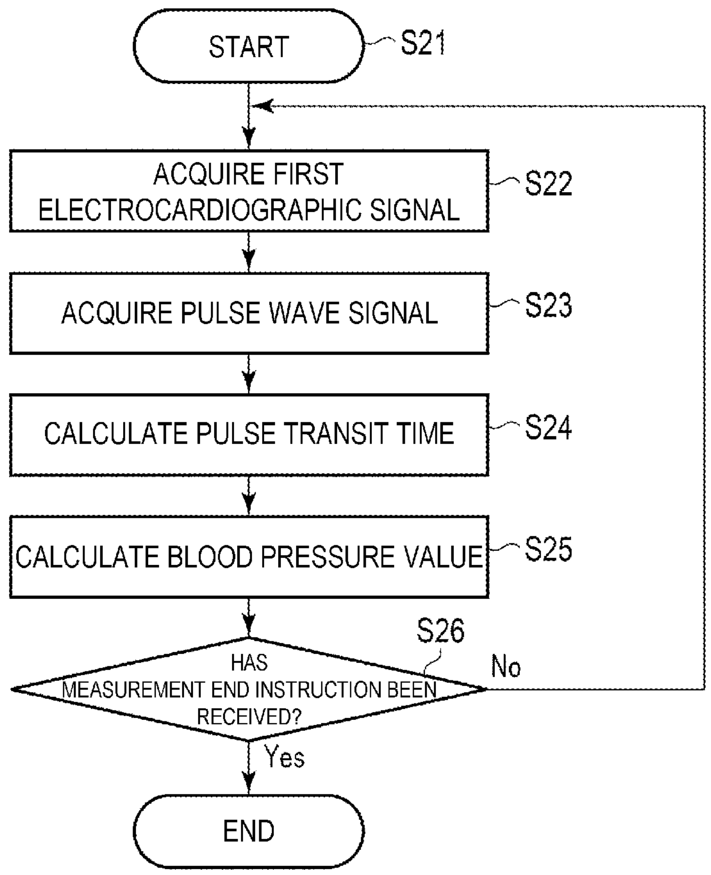
FIG. 10 is a flowchart illustrating operation in which the blood pressure measurement device illustrated in FIG. 1 performs blood pressure measurement based on a pulse transit time.

FIG. 10 illustrates an operation flow when the blood pressure measurement device 10 performs blood pressure measurement based on the pulse transit time.

In step S21 in FIG. 10, the control unit 501 starts blood pressure measurement based on the pulse transit time. For example, the control unit 501 starts blood pressure measurement in response to receiving an operation signal from the operation unit 221 indicating that the user has instructed to start the blood pressure measurement based on the pulse transit time. Additionally, the control unit 501 may start the blood pressure measurement based on the pulse transit time in response to the completion of calibration of the blood pressure calculation formula.

In step S22, the control unit 501 operates as the first electrocardiographic signal measurement control unit 601 and acquires the first electrocardiographic signal using the two optimal internal electrodes 312. In step S23, the control unit 501 operates as the pulse wave measurement control unit 606 and acquires the pulse wave signal using the pulse wave sensor. The processing of step S21 and the processing of step S22 are executed in parallel.

In step S24, the control unit 501 operates as the pulse transit time calculation unit 37 and calculates the pulse transit time on the basis of the first electrocardiographic signal acquired in step S22, the pulse wave signal acquired in step S23, and the feature amount parameter obtained by the processing illustrated in FIG. 9. For example, the control unit 501 detects the R-wave peak point of the first electrocardiographic signal using the feature amount parameter and calculates a time difference between the detected R-wave peak point and the rising point of the pulse wave signal as the pulse transit time.

In step S25, the control unit 501 operates as the blood pressure value calculation unit 38 and calculates a blood pressure value from the pulse transit time calculated in step S24 using the blood pressure calculation Formula (1) described above. The control unit 501 stores the calculated blood pressure value in the storage unit 505 in association with time information.

In step S26, the control unit 501 determines whether an operation signal indicating that the user has instructed to end the blood pressure measurement based on the pulse transit time has been received from the operation unit 221. The processes of steps S22 to S25 are repeated until the control unit 501 receives the operation signal. Thus, the blood pressure value for each beat is recorded. When the control unit 501 receives the operation signal, the control unit 501 ends the blood pressure measurement based on the pulse transit time.

With the blood pressure measurement based on the pulse transit time, the blood pressure can be continuously measured over an extended period of time with a reduced physical burden on the user.

Blood Pressure Measurement Using Oscillometric Method

Figure 11:
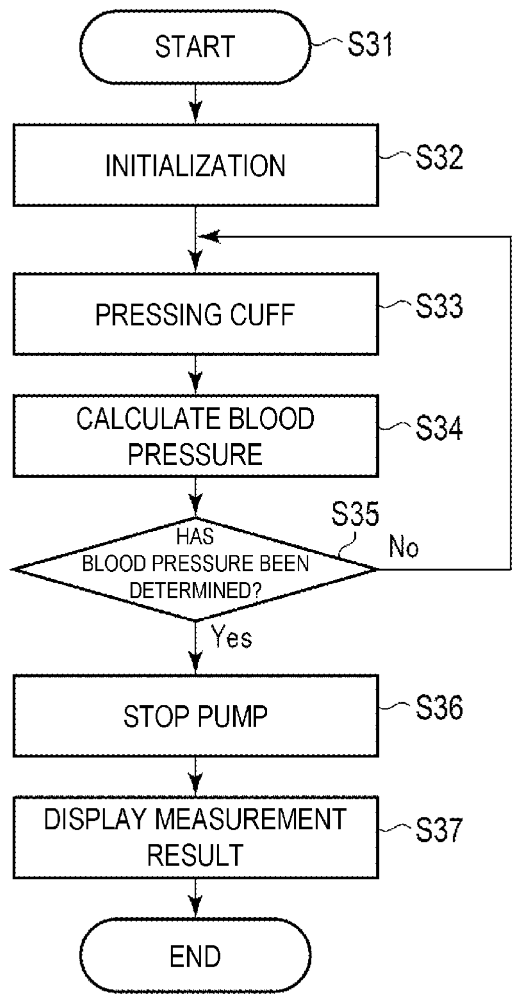
FIG. 11 is a flowchart illustrating operation in which the blood pressure measurement device illustrated in FIG. 1 performs blood pressure measurement using an oscillometric method.

FIG. 11 illustrates an operation flow when the blood pressure measurement device 10 performs blood pressure measurement using the oscillometric method. In the blood pressure measurement using the oscillometric method, the pressing cuff 401 is gradually pressurized and then depressurized. In such a pressurization or depressurization process, the pulse transit time fails to be measured correctly. Thus, during the execution of the blood pressure measurement using the oscillometric method, the blood pressure measurement based on the pulse transit time illustrated in FIG. 10 may be temporarily stopped.

In step S31 of FIG. 11, the control unit 501 starts blood pressure measurement using the oscillometric method. For example, the control unit 501 starts blood pressure measurement in response to receiving an operation signal from the operation unit 221 indicating that the user has instructed to execute blood pressure measurement using the oscillometric method.

In step S32, the control unit 501 operates as the blood pressure measurement control unit 611 to perform initialization for the blood pressure measurement. For example, the control unit 501 initializes a processing memory area. Further, the control unit 501 stops the pump 403 via the pump drive circuit 406. Along with this, the valve 404 is opened, and the air in the pressing cuff 401 is exhausted. The control unit 501 sets an output value at the present time of the pressure sensor 402 as a reference value.

Figure 12:
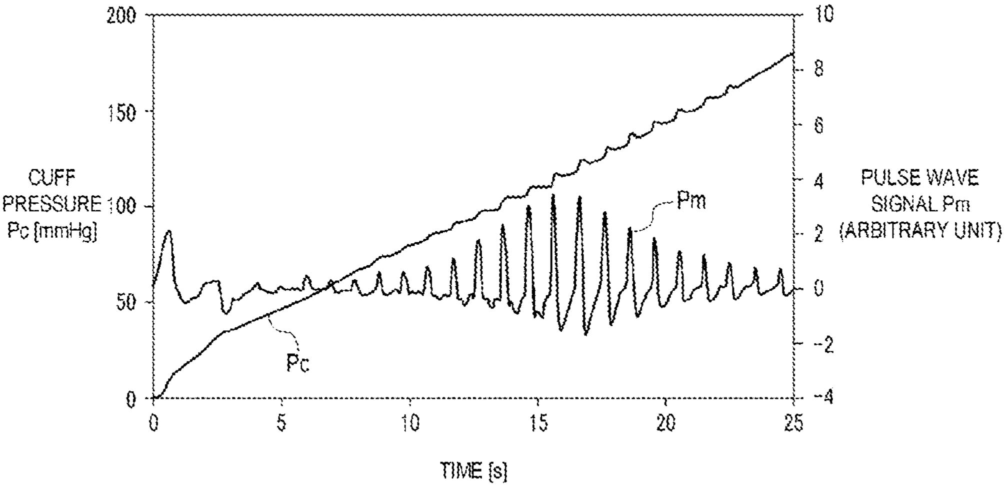
FIG. 12 is a diagram illustrating changes in cuff pressure and pulse wave signal during blood pressure measurement using the oscillometric method.

In step S33, the control unit 501 operates as the blood pressure measurement control unit 611 to perform control of pressurizing the pressing cuff 401. For example, the control unit 501 drives the pump 403 via the pump drive circuit 406. Along with this, the valve 404 is closed and air is supplied to the pressing cuff 401. As a result, the pressing cuff 401 is inflated, and a cuff pressure Pc gradually increases as illustrated in FIG. 12. The control unit 501 monitors the cuff pressure Pc using the pressure sensor 402 and acquires a pulse wave signal Pm representing a fluctuation component of an arterial volume.

In step S34, the control unit 501 operates as the blood pressure measurement control unit 611 and attempts to calculate the blood pressure value (including the SBP and the DBP) on the basis of the pulse wave signal Pm acquired at that point in time. In a case where the blood pressure value fails to be calculated due to lack of data at this point in time (No in step S35), the processing of steps S33 and S34 is repeated as long as the cuff pressure Pc does not reach an upper limit pressure. The upper limit pressure is predetermined from the viewpoint of safety. The upper limit pressure is set to 300 mmHg, for example.

In a case where the blood pressure value can be calculated (Yes in step S35), the processing proceeds to step S36. In step S36, the control unit 501 operates as the blood pressure measurement control unit 611 and stops the pump 403 via the pump drive circuit 406. Along with this, the valve 404 is opened, and the air in the pressing cuff 401 is exhausted.

In step S37, the control unit 501 displays blood pressure measurement results on the display unit 222 and records the blood pressure measurement results in the storage unit 505.

Note that the processing procedure illustrated in FIG. 9, 10, or 11 is an example, and the processing order or the content of each processing can be changed as appropriate. For example, in the blood pressure measurement using the oscillometric method illustrated in FIG. 11, the calculation of blood pressure values may be executed in the depressurization process in which air is discharged from the pressing cuff 401.

Effects

As described above, in the blood pressure measurement device 10 according to the present embodiment, the internal electrode group 31, the external electrode 32, and the impedance measurement unit 361 are provided on the belt 21. Thus, by simply winding the belt 21 around the upper left arm, the internal electrode group 31, the external electrode 32, and the impedance measurement unit 361 can be attached to the user. Thus, the blood pressure measurement device 10 can be easily attached to the user.

The blood pressure measurement device 10 calculates the feature amount parameter related to the waveform feature points of the first electrocardiographic signal acquired using the internal electrode group 31 on the basis of the second electrocardiographic signal acquired using the external electrode 32. When measuring the pulse transit time, the blood pressure measurement device 10 acquires the first electrocardiographic signal and the pulse wave signal, detects the R-wave peak point of the first electrocardiographic signal using the feature amount parameter, and calculates a time difference between the detected R-wave peak point and the rising point of the pulse wave signal as the pulse transit time. The use of the feature amount parameter enables the R-wave peak point of the first electrocardiographic signal to be detected correctly. As a result, the pulse transit time can be measured more accurately. Furthermore, blood pressure can be more accurately measured in blood pressure measurement based on the pulse transit time.

One internal electrode of the internal electrode group 31 is used for acquiring the second electrocardiographic signal. As a result, there is no need to provide a dedicated electrode for acquiring the second electrocardiographic signal, which makes it possible to reduce the manufacturing cost.

The first electrocardiographic signal is acquired using two first electrodes that provide the first electrocardiographic signal having the greatest R-wave amplitude, selected from the internal electrode group 31. As a result, it is possible to identify the time of the R-wave peak point of the first electrocardiographic signal and to measure the pulse transit time more accurately.

A peak point corresponding to the R-wave is used as the waveform feature point of the electrocardiographic signal. Since the R-wave appears more clearly than the Q-wave or the S-wave, the time of the R-wave peak point can be identified more accurately. As a result, the feature amount parameter can be calculated with high accuracy.

The blood pressure calculation formula used in the first blood pressure measurement unit 30 needs to be calibrated on the basis of the blood pressure value acquired by a measurement system different from that of the first blood pressure measurement unit 30. In the present embodiment, the second blood pressure measurement unit 40 is integrated with the first blood pressure measurement unit 30, and the blood pressure calculation formula is calibrated on the basis of the blood pressure value obtained by the second blood pressure measurement unit 40. As a result, the blood pressure calculation formula can be calibrated by the blood pressure measurement device 10 alone. For this reason, the blood pressure calculation formula can be calibrated easily.

Since the blood pressure measurement based on the pulse transit time and the blood pressure measurement using the oscillometric method can be performed by one device, the user's convenience is improved.

Modified Example

The present invention is not limited to the above embodiment.

In the embodiment described above, one of the internal electrodes is used for acquiring the first electrocardiographic signal and the second electrocardiographic signal. Instead of this, a dedicated internal electrode may be provided on the inner circumferential surface of the belt unit 20 to measure the second electrocardiographic signal.

In the embodiment described above, the pulse wave sensor employs an impedance method in which a change in impedance resulting from a change in volume of the artery is detected. Also, the pulse wave sensor may adopt another measurement method such as a photoelectric method, a piezoelectric method, or a radio wave method. In an embodiment employing the photoelectric method, the pulse wave sensor includes: a light emitting element that radiates light toward the artery passing through a target measurement site; and a photodetector for detecting reflected light or transmitted light of the light, and the pulse wave sensor detects a change in light intensity resulting from a change in volume of the artery. In an embodiment employing the piezoelectric method, the pulse wave sensor includes a piezoelectric element provided on the belt to be in contact with the target measurement site and detects a change in pressure resulting from a change in volume of the artery. In an embodiment employing a radio wave method, the pulse wave sensor includes: a transmission element that transmits a radio wave toward the artery passing through a target measurement site and a receiving element that receives a reflection wave of the radio wave, and the pulse wave sensor detects a phase shift between the transmission wave and the reflection wave associated with the change in volume of the artery.

The blood pressure measurement device 10 may further include a pressing cuff, a pump that supplies air to the pressing cuff, a pump drive circuit that drives the pump, and a pressure sensor that detects pressure in the pressing cuff in order to adjust the contact state between the internal electrode 312 and the upper left arm. This pressing cuff is provided at the central end portion 218A of the belt 21. In this case, the pressing cuff 401 is provided in the intermediate portion 218B of the belt 21, for example.

The blood pressure measurement device 10 may further include a pressing cuff, a pump that supplies air to the pressing cuff, a pump drive circuit that drives the pump, and a pressure sensor for detecting the pressure in the pressing cuff in order to adjust the contact state between the sensor unit 362 of the impedance measurement unit 361 and the upper left arm. This pressing cuff is provided at the peripheral end portion 218C of the belt 21. In this case, the pressing cuff 401 is provided in the intermediate portion 218B of the belt 21, for example.

The external electrode 32 may be provided in a start button that initiates the blood pressure measurement (blood pressure measurement by the second blood pressure measurement unit 40) using the oscillometric method, included in the operation unit 221. For example, the start button is formed of a conductive material and the start button serves as the external electrode 32. When the user depresses the start button, the blood pressure measurement using the oscillometric method starts. At this time, since the user is in touch with the external electrode 32, it is possible to acquire the electrocardiographic signal by the first lead, and it is possible to calculate the feature amount parameter. Thus, the feature amount parameter can be calculated at the same time as the blood pressure measurement using the oscillometric method is performed. In addition, the blood pressure calculation formula may be calibrated using the blood pressure values obtained by performing the blood pressure measurement using the oscillometric method. That is, the feature amount parameter can be calculated at the same time as the blood pressure calculation formula is calibrated.

The blood pressure measurement device 10 may not include the second blood pressure measurement unit 40. In an embodiment in which the blood pressure measurement device 10 does not include the second blood pressure measurement unit 40, a blood pressure value obtained by measurement with another blood pressure monitor needs to be input to the blood pressure measurement device 10 for calibration of the blood pressure calculation formula.

A portion of the blood pressure measurement device involved in the measurement of the pulse transit time may be implemented as a single device. In an embodiment, a pulse transit time measurement device including the belt unit 20, the internal electrode group 31, the external electrode 32, the first electrocardiographic signal acquisition unit 33, the second electrocardiographic signal acquisition unit, 34, the feature amount parameter calculation unit 35, the pulse wave signal acquisition unit 36, and the pulse transit time calculation unit 37 is provided. For example, the pulse transit time measurement device may transmit the measurement result of the pulse transit time to an external device, and the external device may calculate a blood pressure value from the measurement result of the pulse transit time.

The target measurement site is not limited to the upper arm and may be another site such as the wrist, thigh, or ankle in which the pulse wave signal can be acquired.

The present invention is not limited to the embodiment described above as is and can be embodied by modifying the constituent elements within a range not departing from the gist of the invention in an implementation stage. Further, various inventions can be formed by appropriately combining a plurality of constituent elements disclosed in the embodiment described above. For example, some constituent elements may be omitted from the entire constituent elements illustrated in the embodiment. Furthermore, the constituent elements of different embodiments may be combined appropriately.

REFERENCE SIGNS LIST

10 Blood pressure measurement device
20 Belt unit
21 Belt
22 Body
210A Inner cloth
210B Outer cloth
211 Outer circumferential surface
212 Inner circumferential surface
213 Loop surface
214 Hook surface
221 Operation unit
222 Display unit
30 First blood pressure measurement unit
31 Internal electrode group
32 External electrode
33 First electrocardiographic signal acquisition unit
34 Second electrocardiographic signal acquisition unit
35 Feature amount parameter calculation unit
36 Pulse wave signal acquisition unit
37 Pulse transit time calculation unit
38 Blood pressure value calculation unit
312 Internal electrode
333 Switch circuit
334 Subtraction circuit
335 AFE
344 Subtraction circuit
345 AFE
361 Impedance measurement unit
362 Sensor unit
362A to 362D Electrode
363 Energization and voltage detection circuit
40 Second blood pressure measurement unit
401 Pressing cuff
402 Pressure sensor
403 Pump
404 Valve
405 Oscillation circuit
406 Pump drive circuit
501 Control unit
502 CPU
503 RAM
504 ROM
505 Storage unit
506 Battery
507 Communication unit
601 First electrocardiographic signal measurement control unit 602 First electrocardiographic signal storage unit
603 Second electrocardiographic signal measurement control unit
604 Second electrocardiographic signal storage unit
606 Pulse wave measurement control unit
607 Pulse wave signal storage unit
610 First blood pressure value storage unit
611 Blood pressure measurement control unit
612 Second blood pressure value storage unit
613 Display control unit
614 Instruction input unit
615 Calibration unit
70 Upper left arm
71 Humerus
72 Brachial artery

The invention claimed is:

1. A pulse transit time measurement device comprising:

a belt unit configured to be wound around a target measurement site of a user;

a plurality of first electrodes provided on an inner circumferential surface of the belt unit;

a second electrode provided on the inner circumferential surface of the belt unit;

a third electrode provided on an outer circumferential surface of the belt unit;

a first electrocardiographic signal measurement circuit configured to measure a first electrocardiographic signal of the user based on a potential difference between two first electrodes selected from the plurality of first electrodes;

a second electrocardiographic signal measurement circuit configured to measure a second electrocardiographic signal of the user based on a potential difference between the second electrode and the third electrode;

a pulse wave signal acquisition circuit including a pulse wave sensor provided in the belt unit and configured to acquire a pulse wave signal representing a pulse wave of the user using the pulse wave sensor; and a processor coupled to the first electrocardiographic signal measurement circuit and the second electrocardiographic signal measurement circuit, the processor being configured to:

simultaneously receive the first and second electrocardiographic signals measured respectively by the first and second electrocardiographic signal measurement circuits;

detect a waveform feature point of the second electrocardiographic signal in a predetermined time period;

determine a time range including a time of the waveform feature point of the second electrocardiographic signal, the time of the waveform feature point of the second electrocardiographic signal being at a center of the time range;

detect a waveform feature point of the first electrocardiographic signal in the time range;

calculate a feature amount parameter based upon the waveform feature point of the first electrocardiographic signal; and calculate a pulse transit time based on a time difference between the detected waveform feature point of the first electrocardiographic signal and a waveform feature point of the pulse wave signal.

2. The pulse transit time measurement device according to claim 1, wherein the processor is configured to detect a peak with a maximum amplitude of the first electrocardiographic signal measured in the time range, and acquire an amplitude value of the peak that is detected or a sign of the amplitude value as the feature amount parameter.

3. The pulse transit time measurement device according to claim 1, wherein the second electrode is one of the plurality of first electrodes.

4. The pulse transit time measurement device according to claim 1, wherein the processor is further configured to select the two first electrodes that provide the first electrocardiographic signal having a greatest amplitude of an R-wave among the plurality of first electrodes.

5. A blood pressure measurement device comprising:

the pulse transit time measurement device according claim 1, wherein the processor is further configured to calculate a first blood pressure value based on the pulse transit time that is calculated.

6. The blood pressure measurement device according to claim 5, further comprising:

a pressing cuff provided in the belt unit;

a fluid supply unit supplying a fluid to the pressing cuff; and a pressure sensor detecting pressure in the pressing cuff, wherein the processor is further configured to calculate a second blood pressure value based on an output of the pressure sensor.

7. The blood pressure measurement device according to claim 6, further comprising a button for initiating blood pressure measurement by the pressing cuff, the fluid supply unit, the pressure sensor, and the processor, wherein the third electrode is provided on the button.

8. The pulse transit time measurement device according to claim 2, wherein the second electrode is one of the plurality of first electrodes.

9. The pulse transit time measurement device according to claim 2, wherein the processor is further configured to select the two first electrodes that provide the first electrocardiographic signal having a greatest amplitude of an R-wave among the plurality of first electrodes.

10. The pulse transit time measurement device according to claim 3, wherein the processor is further configured to select the two first electrodes that provide the first electrocardiographic signal having a greatest amplitude of an R-wave among the plurality of first electrodes.

11. The pulse transit time measurement device according to claim 8, wherein the processor is further configured to select the two first electrodes that provide the first electrocardiographic signal having a greatest amplitude of an R-wave among the plurality of first electrodes.

12. A blood pressure measurement device comprising:

the pulse transit time measurement device according to claim 2, wherein the processor is further configured to calculate a first blood pressure value based on the pulse transit time that is calculated.

13. A blood pressure measurement device comprising:

the pulse transit time measurement device according to claim 3, wherein the processor is further configured to calculate a first blood pressure value based on the pulse transit time that is calculated.

14. A blood pressure measurement device comprising:

the pulse transit time measurement device according to claim 4, wherein the processor is further configured to calculate a first blood pressure value based on the pulse transit time that is calculated.

15. A blood pressure measurement device comprising:

the pulse transit time measurement device according to claim 8, wherein the processor is further configured to calculate a first blood pressure value based on the pulse transit time that is calculated.

16. A blood pressure measurement device comprising:

the pulse transit time measurement device according to claim 9, wherein the processor is further configured to calculate a first blood pressure value based on the pulse transit time that is calculated.

17. A blood pressure measurement device comprising:

the pulse transit time measurement device according to claim 10, wherein the processor is further configured to calculate a first blood pressure value based on the pulse transit time that is calculated.

18. A blood pressure measurement device comprising:

the pulse transit time measurement device according to claim 11, wherein the processor is further configured to calculate a first blood pressure value based on the pulse transit time that is calculated.

19. The blood pressure measurement device according to claim 12, further comprising:

a pressing cuff provided in the belt unit;

a fluid supply unit supplying a fluid to the pressing cuff; and a pressure sensor detecting pressure in the pressing cuff, wherein the processor is further configured to calculate a second blood pressure value based on an output of the pressure sensor.

20. The blood pressure measurement device according to claim 13, further comprising:

a pressing cuff provided in the belt unit;

a fluid supply unit supplying a fluid to the pressing cuff; and a pressure sensor detecting pressure in the pressing cuff, wherein the processor is further configured to calculate a second blood pressure value based on an output of the pressure sensor.

21. The pulse transit time measurement device according to claim 1, wherein the second electrocardiographic signal measurement circuit is configured to measure the second electrocardiographic signal of the user based on the potential difference between the second electrode and the third electrode with a measurement method capable of measuring more accurate electrocardiographic signals than a measurement method of the first electrocardiographic signal measurement circuit.

22. The pulse transit time measurement device according to claim 1, wherein the belt unit is configured to be wound around one of arms of the user corresponding to the target measurement site of the user, the first electrocardiographic signal measurement circuit is configured to measure the first electrocardiographic signal of the user based on the potential difference between the two first electrodes selected from the plurality of first electrodes in a state in which the two first electrodes are in contact with the one of the arms of the user, and the second electrocardiographic signal measurement circuit is configured to measure the second electrocardiographic signal of the user based on the potential difference between the second electrode and the third electrode in a state in which the second electrode is in contact with the one of the arms of the user and the third electrode is in contact with another one of the arms of the user.

* * * * *